(12) United States Patent
Bardon et al.

(10) Patent No.: US 11,332,484 B2
(45) Date of Patent: May 17, 2022

(54) VOLTAGE SENSITIVE DYES

(71) Applicant: Akita Innovations LLC, Billerica, MA (US)

(72) Inventors: Kevin M. Bardon, Somerville, MA (US); Richard A. Minns, Arlington, MA (US); Scott D. Selfridge, Hudson, NH (US); Larry Takiff, Woburn, MA (US); Timothy Adams, Howell, NJ (US)

(73) Assignee: Akita Innovations LLC, Billerica, MA (US)

( * ) Notice: Subject to any disclaimer, the term of this patent is extended or adjusted under 35 U.S.C. 154(b) by 0 days.

(21) Appl. No.: 16/490,467

(22) PCT Filed: Mar. 2, 2018

(86) PCT No.: PCT/US2018/020621
§ 371 (c)(1),
(2) Date: Aug. 30, 2019

(87) PCT Pub. No.: WO2018/217266
PCT Pub. Date: Nov. 29, 2018

(65) Prior Publication Data
US 2020/0071342 A1    Mar. 5, 2020

Related U.S. Application Data

(63) Continuation of application No. 15/448,398, filed on Mar. 2, 2017, now abandoned.

(51) Int. Cl.
| | | |
|---|---|---|
| *C07F 5/02* | (2006.01) | |
| *A61B 5/00* | (2006.01) | |
| *A61K 49/00* | (2006.01) | |
| *C09K 11/06* | (2006.01) | |

(52) U.S. Cl.
CPC ............ *C07F 5/022* (2013.01); *A61B 5/0071* (2013.01); *A61K 49/006* (2013.01); *A61K 49/0017* (2013.01); *C09K 11/06* (2013.01); *C09K 2211/1029* (2013.01)

(58) Field of Classification Search
CPC ... C07F 5/022; A61B 5/0071; A61K 49/0017; A61K 49/006; C09K 11/06; C09K 2211/1029
See application file for complete search history.

(56) References Cited

U.S. PATENT DOCUMENTS

| | | | |
|---|---|---|---|
| 6,107,066 | A | 8/2000 | Tsien et al. |
| 6,166,853 | A | 12/2000 | Sapia et al. |
| 8,129,532 | B2 | 3/2012 | Loew et al. |
| 8,155,730 | B2 | 4/2012 | Pertsov et al. |
| 8,993,258 | B2 | 3/2015 | Yan et al. |
| 9,357,924 | B2 | 6/2016 | Pertsov et al. |
| 9,636,424 | B2 | 5/2017 | Pertsov et al. |
| 2008/0097222 | A1 | 4/2008 | Pertsov et al. |
| 2009/0042227 | A1 | 2/2009 | Loew et al. |
| 2012/0196893 | A1 | 8/2012 | Pertsov et al. |
| 2013/0189185 | A1 | 7/2013 | Li et al. |
| 2013/0330762 | A1 | 12/2013 | Yan et al. |
| 2015/0291628 | A1 | 10/2015 | Danaboyina et al. |
| 2016/0256576 | A1 | 9/2016 | Pertsov et al. |

FOREIGN PATENT DOCUMENTS

| | | |
|---|---|---|
| CN | 105001856 A | 10/2015 |
| WO | WO 2012/173575 A1 | 12/2012 |

OTHER PUBLICATIONS

Ma et al., J. Mater. Chem. C, 2014, 2, 3900-3913.*
STN Registry database entry for CAS RN 1361027-53-3, entry date Mar. 15, 2012, Accessed Mar. 27, 2021.*
STN Registry database entry for CAS RN 1391970-66-3, entry date Aug. 21, 2012, Accessed Mar. 27, 2021.*
International Search Report and Written Opinion dated Oct. 30, 2018 in connection with Application No. PCT/US2018/020621.
International Preliminary Report on Patentability dated Sep. 12, 2019 in connection with Application No. PCT/US2018/020621.
[No Author Listed], American Chemical Society, Sci Finder Database Entries 77. 946114-27-8; 78. 946074-76-6 (Component: 946114-27-8); 85.1141557-29-0; 87. 1141450-86-3 (Component: 1141557-29-0). 112. 1356156-30-3; 119. 1221790-65-3; 131. 1618699-38-9; 139. 1357927-61-7; 140. 1446343-41-4, accessed online Feb. 19, 2016, 1 page.
[No Author Listed], American Chemical Society, Sci Finder Database Entries 145. 1356057-54-9; 150. 1355975-23-3 (Component: 1356057-54-9); 152. 1809509-94-1; 161. 1048032-36-5 (Component: 1064778-23-9); 171. 1444103-48-3; 172. 1357927-62-8, accessed online Feb. 19, 2016, 1 page.

(Continued)

*Primary Examiner* — Alicia L Otton
(74) *Attorney, Agent, or Firm* — Wolf, Greenfield & Sacks, P.C.

(57) ABSTRACT

Voltage sensitive dyes comprising boron and related compositions and methods are provided. In some embodiments, a voltage sensitive dye comprises an electron acceptor comprising boron. The electron acceptor may be attached (e.g., covalently) to at least one electron donating group and at least one polar group. For instance, the electron acceptor may comprise optionally substituted boron dipyrromethene (e.g., optionally substituted 4,4-difluoro-4-bora-3a,4a-diaza-s-indacene). The point of attachment and chemical nature of the electron donating group(s) and polar group(s) may be selected to impart beneficial properties to the voltage sensitive dye. For instance, the voltage sensitive dye may have an extended difference in the dipole moment between the ground and electronic states due at least in part to the position of the electron donating group(s). The voltage sensitive dyes, described herein, may have high specificity, high signal to noise ratio, fast responsivity, high voltage sensitivity, high photostability, and/or high brightness.

7 Claims, 2 Drawing Sheets

(56) References Cited

OTHER PUBLICATIONS

[No Author Listed], American Chemical Society, Sci Finder Database Entries 173. 1443982-50-0 (Component: 1444103-48-3); 183. 1197220-49-7; 188. 1197180-40-7 (Component: 1197220-49-7); 203. 1643132-00-6; 211. 1431883-23-6; 214. 1446343-42-5; 219. 1221790-66-4; 225. 1643132-02-8; 232. 1237696-64-8, accessed online Feb. 19, 2016, 1 page.
[No Author Listed], American Chemical Society, Sci Finder Database Entries 233.1661005-13-5; 236. 1491141-80-0; 244. 1620842-33-2; 256. 1056003-42-9; 266. 1809509-95-2; 269. 1643132-01-7; 286. 1643131-96-7; 287. 1355975-17-5 (Component: 1356057-53-8); 301. 1608488-46-5 (Component: 1608618-72-9), accessed online Feb. 19, 2016, 1 page.
[No Author Listed], American Chemical Society, Sci Finder Database Entries 352. 1629684-09-8 (Component: 1629849-66-6); 356. 1629849-67-7; 358. 1629684-11-2 (Component: 1629849-67-7)), accessed online Feb. 19, 2016, 1 page.
[No Author Listed], American Chemical Society, Sci Finder Database Entries 360.1629849-68-8; 361. 1629684-18-9 (Component: 1629849-68-8); 366. 1629684-20-3 (Component: 1629849-69-9), accessed online Feb. 19, 2016, 1 page.
[No Author Listed], American Chemical Society, Sci Finder Database Entries 1. 1374676-70-6; 2. 1374676-71-7; 3. 1374676-74-0; 4. 816457-15-5; 5. 1692887-00-5; 6. 1374676-75-1; 7. 1630909-47-5; 8. 1630909-57-7; 9. 1630909-54-4, accessed online Feb. 19, 2016, 1 page.
[No Author Listed], American Chemical Society, Sci Finder Database Entries 10.1630909-52-2; 11. 1630909-58-8; 12. 1242274-63-0, accessed online Feb. 19, 2016, 1 page.
[No Author Listed], American Chemical Society, Sci Finder Database Entries 1. 1542150-33-3; 2. 1542150-48-0, accessed online Feb. 19, 2016, 1 page.
[No Author Listed], American Chemical Society, Sci Finder Database Entries 1. 1417037-14-9; 2. 1417164-24-9; 3. 1542150-39-9, accessed online Feb. 19, 2016, 1 page.
[No Author Listed], American Chemical Society, Sci Finder Database Entries 4. 1417037-15-0; 5. 1639351-70-4 6. 1417164-25-0; 7. 1446889-80-0; 8. 1403231-28-6; 9. 1542150-42-4, accessed online Feb. 19, 2016, 1 page.
[No Author Listed], American Chemical Society, Sci Finder Database Entries 10. 1448551-92-5; 11. 1446889-74-2; 12. 1204193-20-3; 13. 1542150-46-8; 14. 1542150-63-9 15. 1639351-71-5; 16. 1446889-77-5; 17. 1403231-29-7; 18. 1542150-37-7, accessed online Feb. 19, 2016, 1 page.
[No Author Listed], American Chemical Society, Sci Finder Database Entries 19. 1542150-69-5; 20. 1542150-34-4; 21. 1542150-40-2; 22. 1204193-21-4; 23. 1542150-36-6; 24. 1639351-72-6; 25. 1542150-32-2; 26. 1542150-87-7; 27. 1446889-86-6 , accessed online Feb. 19, 2016, 1 page.
[No Author Listed], American Chemical Society, Sci Finder Database Entries 28. 1403231-31-1; 29. 1446890-02-3; 30. 1586735-81-0; 31. 1542150-66-2; 32. 1403231-30-0; 33. 1446889-83-3; 34. 1446890-00-1; 35. 1446889-98-0; 36. 1448551-93-6, accessed online Feb. 19, 2016, 1 page.
[No Author Listed], American Chemical Society, Sci Finder Database Entries 37. 1448551-94-7; 38. 1617544-44-1; 39. 1621604-98-5; 40. 1617544-46-3; 41. 1617544-47-4; 42. 1446889-92-4, accessed online Feb. 19, 2016, 1 page.
[No Author Listed], American Chemical Society, Sci Finder Database Entries 43. 1446889-89-9; 44. 1446889-95-7, accessed online Feb. 19, 2016, 1 page.
[No Author Listed], NCBI/NIH, PubChem Accession No. 101426289. Dec. 18, 2015. Retrieved from the internet. 10 pages.
[No Author Listed], NCBI/NIH, PubChem Accession No. 102184376. Dec. 24, 2015. Retrieved from the internet. 8 pages.
Bai et al., Low molecular weight Neutral Boron Dipyrromethene (Bodipy) dyads for fluorescence-based neural imaging. J Molecular Structure. May 2014;1065-1066:10-15.
Deal et al., Isomerically pure tetramethylrhodamine voltage reporters. J Am Chem Soc. Jul. 27, 2016;138(29):9085-8. doi: 10.1021/jacs.6b05672. Epub Jul. 18, 2016.
Engel et al., Polycations. 18. The synthesis of polycationic lipid materials based on the diamine 1,4-diazabicyclo[2.2.2]octane. Chem Phys Lipids. Mar. 2009;158(1):61-9. doi: 10.1016/j.chemphyslip. 2008.12.003. Epub Dec. 25, 2008.
Huang et al., A photostable silicon rhodamine platform for optical voltage sensing. J Am Chem Soc. Aug. 26, 2015;137(33):10767-76. doi: 10.1021/jacs.5b06644. Epub Aug. 13, 2015.
Li et al., Syntheses and spectral properties of functionalized, water-soluble BODIPY derivatives. J Org Chem. Mar. 7, 2008;73(5):1963-70.
Liu et al., Targeting β-amyloid plaques and oligomers: development of near-IR fluorescence imaging probes. Future Med Chem. Feb. 2017;9(2):179-198. doi: 10.4155/fmc-2016-0185. Epub Jan. 27, 2017.
Loew, Design and use of organic voltage sensitive dyes. Ch 2 in Membrane Potential Imaging in the Nervous System: Methods and Applications, pp. 13-23, Canepari et al. (eds). Springer, New York, Sep. 2010.
Miller et al., Optically monitoring voltage in neurons by photo-induced electron transfer through molecular wires. Proc Natl Acad Sci U S A. Feb. 7, 2012;109(6):2114-9. doi: 10.1073/pnas. 1120694109. Epub Jan. 24, 2012.
Peterka et al., Imaging voltage in neurons. Neuron. Jan. 13, 2011;69(1):9-21. doi: 10.1016/j.neuron.2010.12.010.
Preuss et al., Comparison of two voltage-sensitive dyes and their suitability for long-term imaging of neuronal activity. PLoS One. Oct. 4, 2013;8(10):e75678, 1-12. doi: 10.1371/journal.pone. 0075678. eCollection 2013.
Rurack et al., A highly efficient sensor molecule emitting in the near infrared (NIR):3,5-distyryl-8-(p-dimethylaminophenyl)-difluoroboradiaza-s-indancene. New J Chem. 2001;25(2):289-92.
Tahtaoui et al., Convenient method to access new 4,4-dialkoxy- and 4,4-idaryloxy-diaza-s-indacene dyes: synthesis and spectroscopic evaluation. J Org Chem. 2007; 72: 269-72.
Watanabe et al., Molecular imaging of β-amyloid plaques with near-infrared boron dipyrromethane (BODIPY)-based fluorescent probes. Mol Imaging. Jul.-Aug. 2013;12(5):338-47.
Yu et al., Mono- and di(dimethylamino)styryl-substituted borondipyrromethene and boron diindomethene dyes with intense near-infrared fluorescenece. Chem Asian J. 2006; 1-2: 176-87.
Zhang et al., Long-wavelength, photostable, two-photon excitable BODIPY fluorophores readily modifiable for molecular probes. J Org Chem. Sep. 20, 2013;78(18):9153-60. doi: 10.1021/jo401379g. Epub Sep. 11, 2013.
Extended European Search Report for European Application No. EP18805624.6 dated Feb. 15, 2021.
Bio et al., Efficient activation of a visible light-activatable CA4 prodrug through intermolecular photo-unclick chemistry in mitochondria. Chem Commun (Camb). Feb. 7, 2017;53(11):1884-1887. doi: 10.1039/c6cc09994g. Epub Jan. 23, 2017.
Copley et al., Modulating short wavelength fluorescence with long wavelength light. J Am Chem Soc. Aug. 27, 2014;136(34):11994-2003. doi: 10.1021/ja504879p. Epub Aug. 15, 2014.
Godoy et al., Synthesis of a fluorescent BODIPY-tagged ROMP catalyst and initial polymerization-propelled diffusion studies. Tetrahedron. Sep. 2, 2015; 71(35):5965-5972. doi.org/10.1016/j.tet. 2015.04.02.
Kong et al., A highly selective mitochondria-targeting fluorescent K(+) sensor. Angew Chem Int Ed Engl. Oct. 5, 2015;54(41):12053-7. doi: 10.1002/anie.201506038. Epub Aug. 21, 2015.
Meng et al., pH-Responsive supramolecular vesicles assembled by water-soluble pillar[5] arene and a BODIPY photosensitizer for chemo-photodynamic dual therapy. Chem Commun (Camb). Oct. 1, 2015;51(76):14381-4. doi: 10.1039/c5cc05785j. Epub Aug. 13, 2015.
Niu et al., New insights into the solubilization of Bodipy dyes. Tetrahedron Letters. Jul. 8, 2009; 50(27):3840-3844. doi.org/10. 1016/j.tetlet.2009.04.017.

(56) References Cited

OTHER PUBLICATIONS

Olivier et al., Near-infrared fluorescent nanoparticles formed by self-assembly of lipidic (Bodipy) dyes. Chemistry. Oct. 10, 2011;17(42):11709-14. doi: 10.1002/chem.201101407. Epub Sep. 6, 2011.

\* cited by examiner

VOLTAGE SENSITIVE DYES

GOVERNMENT SPONSORSHIP

This invention was made with Government support under Grant No. D15PC00054, awarded by the Defense Advanced Research Projects Agency. The Government has certain rights in this invention.

RELATED APPLICATIONS

This application is a national stage filing under 35 U.S.C. § 371 of International Patent Application Serial No. PCT/US2018/020621, filed Mar. 2, 2018, entitled "Voltage Sensitive Dyes", which claims the benefit of U.S. patent application Ser. No. 15/448,398, filed Mar. 2, 2017, entitled "Voltage Sensitive Dyes", each of which is incorporated herein by reference in its entirety for all purposes.

TECHNICAL FIELD

Voltage sensitive dyes and related compositions and methods are provided.

BACKGROUND

The movement of charged species across cell membranes drives innumerable cellular functions. Understanding voltages produced by the movement of these charges species will allow advances in cell differentiation, tissue regeneration, and wound healing. Accordingly, much effort has focused on the development of techniques to measure the voltage across cell membranes. Some efforts have focused on the use of electrodes. However, electrodes are often limited by size constraints and placement restrictions. Voltage sensitive dyes, which measure voltage changes in cells via spectral changes of the dye, have emerged that allow for measurements unobtainable with electrodes. However, many voltage sensitive dyes suffer from one or more of the following: low specificity, low signal to noise ratio, slow responsivity, low sensitivity, poor photostability, and limited brightness. Accordingly, improved voltage sensitive dyes, compositions, and methods are needed.

SUMMARY

Voltage sensitive dyes and related composition and methods are provided. The present invention provides compounds, compositions, preparations, formulations, kits, and methods useful for measuring the voltage across cell membranes. More specifically, the present invention relates to compounds, compositions, kits, and methods for measuring the voltage across cell membranes using a voltage sensitive dye comprising boron. The subject matter of the present invention involves, in some cases, interrelated products, alternative solutions to a particular problem, and/or a plurality of different uses of one or more systems and/or articles.

In one set of embodiments, compositions of matter are provided. In one embodiment, a composition of matter comprises a compound of Formula I:

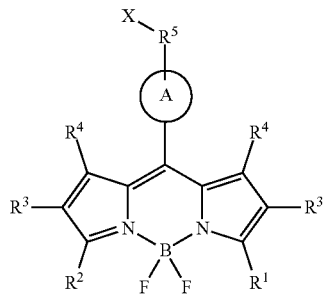

or a salt thereof, wherein:

$R^1$ and $R^2$ are independently hydrogen, optionally substituted alkyl, optionally substituted alkenyl, optionally substituted alkynyl, optionally substituted aryl, optionally substituted heteroaryl, or an electron donating group, provided that at least one of $R^1$ and $R^2$ is an electron donating group;

each $R^3$ is independently hydrogen, optionally substituted alkyl, halo, or a linking group;

each $R^4$ is hydrogen or optionally substituted alkyl;

Ring A is optionally substituted arylene or optionally substituted heteroarylene;

$R^5$ is optionally substituted acylene, optionally substituted alkenylene, optionally substituted alkylene, optionally substituted alkynylene, substituted amino, optionally substituted arylene, optionally substituted heteroalkenylene, optionally substituted heteroalkylene, optionally substituted heteroalkynylene, optionally substituted heteroarylene, —O—, or optionally substituted thiolene; and X is a polar group, wherein X comprises a positively charged moiety, provided that the positively charged moiety is not a metal.

In another embodiment, a composition of matter comprises a compound of Formula I:

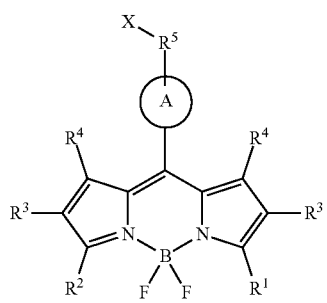

or a salt thereof, wherein:

$R^1$ and $R^2$ are independently hydrogen, optionally substituted alkyl, or an electron donating group, provided that at least one of $R^1$ and $R^2$ is an electron donating group;

each $R^3$ is independently hydrogen, optionally substituted alkyl, halo, or a linking group;

each $R^4$ is hydrogen or optionally substituted alkyl;

Ring A is optionally substituted arylene or optionally substituted heteroarylene;

$R^5$ is optionally substituted acylene, optionally substituted alkenylene, optionally substituted alkylene, optionally substituted alkynylene, substituted amino, optionally substituted arylene, optionally substituted heteroalkenylene, optionally substituted heteroalkylene, optionally substituted heteroalkynylene, optionally substituted heteroarylene, —O—, or optionally substituted thiolene;

X is a polar group, wherein X is charged or has a log(P) of less than or equal to about 0;

the electron donating group is —($R^6$)$_n$—$R^7$:

each $R^6$ is independently optionally substituted alkenylene, optionally substituted alkynylene, optionally substituted arylene, or optionally substituted heteroarylene;

$R^7$ is —N(R")$_2$ or optionally substituted thiol;

each R" is independently $C_{1-12}$ alkyl, provided that at least one R" is $C_{2-12}$alkyl; and n is 1-5. In some embodiments, X is negatively charged. In some embodiments, X is positively charged.

In another set of embodiments, voltage-sensitive dyes are provided. In one embodiment, a voltage-sensitive dye comprises an electron acceptor comprising boron, an electron donating group attached to the electron acceptor, and polar group attached to the electron acceptor, wherein a maximum absorbance wavelength in methanol of the voltage-sensitive dye is greater than or equal to about 600 nm.

In one set of embodiments, methods are provided. In one embodiment, a method comprises exposing a cell membrane to a voltage sensitive dye comprising an electron acceptor comprising boron, an electron donor, and a polar group, wherein a maximum absorbance wavelength in methanol of the voltage-sensitive dye is greater than or equal to about 600 nm.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
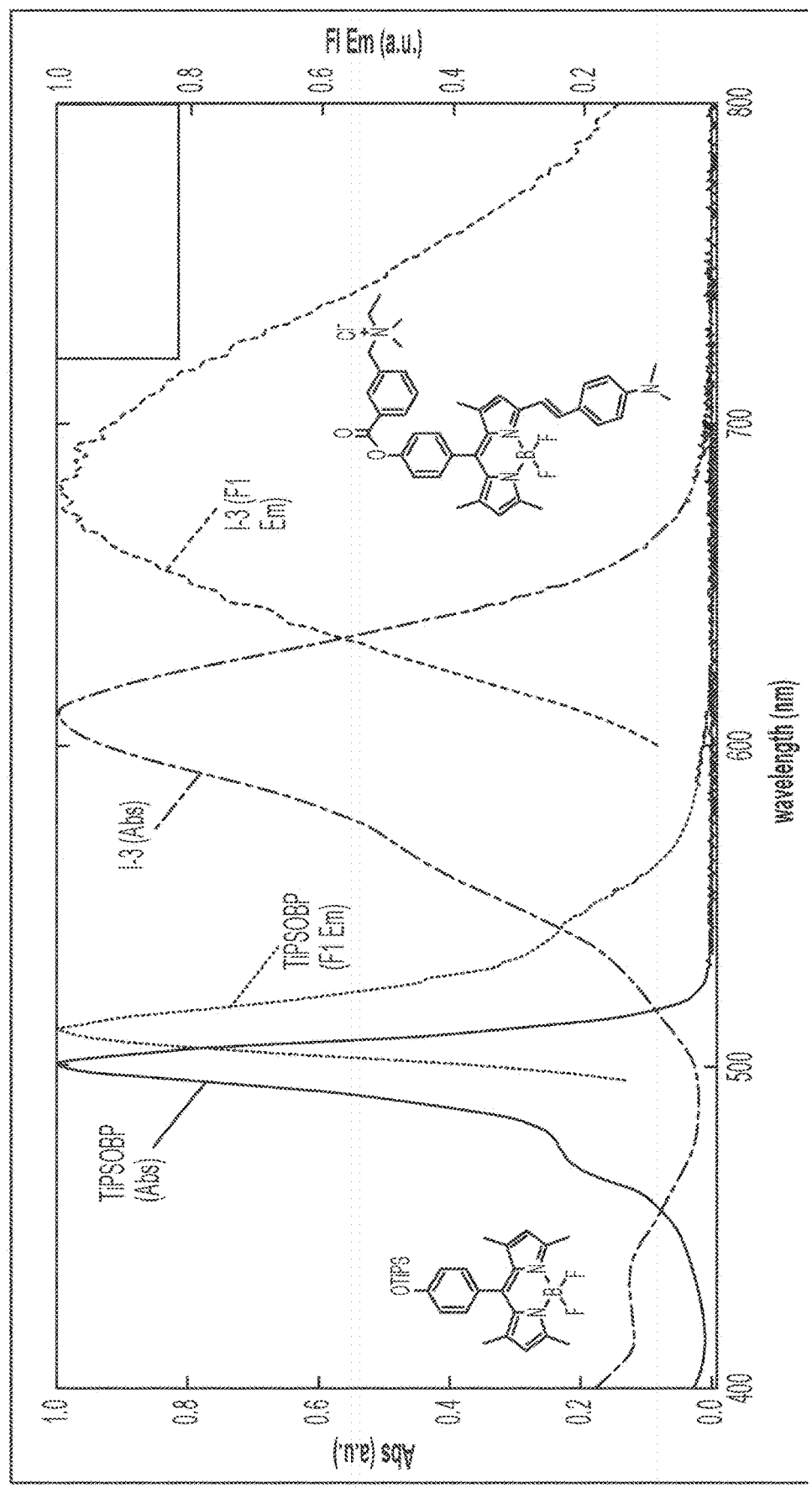
FIG. 1 shows absorbance and emission spectra of a dye, according to certain embodiments.

Voltage sensitive dyes comprising boron and related compositions and methods are provided. In some embodiments, a voltage sensitive dye comprises an electron acceptor comprising boron. The electron acceptor may be attached (e.g., covalently) to at least one electron donating group and at least one polar group. For instance, the electron acceptor may comprise optionally substituted boron dipyrromethene (e.g., optionally substituted 4,4-difluoro-4-bora-3a,4a-diaza-s-indacene). The point of attachment and chemical nature of the electron donating group(s) and polar group(s) may be selected to impart beneficial properties to the voltage sensitive dye. For instance, the voltage sensitive dye may have an extended difference in the dipole moment between the ground and electronic states due at least in part to the position of the electron donating group(s). The position of the polar group may allow the voltage sensitive dye to have a beneficial association with and/or orientation at or in the cell membrane. In certain embodiments, the voltage sensitive dye may comprise one or more additional moieties that impart beneficial properties to the dye. For instance, the voltage sensitive dye may further comprise a biological molecule (e.g., cell-surface targeting moiety) attached to the electron acceptor or the polar group.

The voltage sensitive dyes, described herein, may have high specificity, high signal to noise ratio, fast responsivity, high voltage sensitivity, high photostability, and/or high brightness.

In some embodiments, the voltage sensitive dye comprises Formula (I):

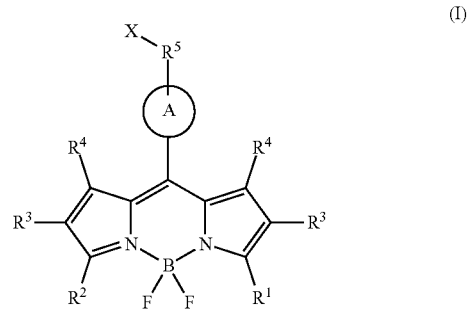

or a salt thereof, wherein:

$R^1$ and $R^2$ are independently hydrogen, optionally substituted alkyl, optionally substituted alkenyl, optionally substituted alkynyl, optionally substituted aryl, optionally substituted heteroaryl, or an electron donating group, provided that at least one of $R^1$ and $R^2$ is an electron donating group;

each $R^3$ is independently hydrogen, optionally substituted alkyl, halo, or a linking group;

each $R^4$ is hydrogen or optionally substituted alkyl;

Ring A is optionally substituted arylene or optionally substituted heteroarylene;

$R^5$ is optionally substituted acylene, optionally substituted alkenylene, optionally substituted alkylene, optionally substituted alkynylene, substituted amino, optionally substituted arylene, optionally substituted heteroalkenylene, optionally substituted heteroalkylene, optionally substituted heteroalkynylene, optionally substituted heteroarylene, —O—, or optionally substituted thiolene; and X is a polar group, wherein X is charged or has a log(P) of less than or equal to about 0.

In some embodiments, at least one of $R^1$ and $R^2$ is an electron donating group. As used herein the term "electron donating group" has its ordinary meaning in the art and may be a functional group that donates some of its electron density into a conjugated π system via resonance or inductive effects. In some embodiments, the electron donating group may have a Hammett sigma constant value of less than about 0 (e.g., less than or equal to about −0.05, less than or equal to about −0.08, less than or equal to about −0.1, less than or equal to about −0.15, less than or equal to about −0.2, less than or equal to about −0.3, less than or equal to about −0.4, less than or equal to about −0.5). In certain embodiments, the electron donating group may be an optionally substituted heteroatom (e.g., nitrogen, oxygen) covalently attached to a conjugated moiety (e.g., aryl, alkenyl, alkynyl, heteroaryl). In certain embodiment, the placement of an electron donating group at $R^1$ and/or $R^2$ may contribute to the extended difference in the dipole moment between the ground and electronic state of the dye and according the relatively high voltage sensitivity of the dye. In some embodiments, $R^1$ is an electron donating group. In some such embodiments, $R^2$ is not an electron donating group. In other instances, $R^1$ is not an electron donating group. In some such embodiments, $R^2$ is an electron donating group. In certain embodiments, $R^1$ and $R^2$ are independently an electron donating group.

In some embodiments, $R^1$ and $R^2$ are independently optionally substituted alkyl (e.g., $C_{1-10}$alkyl, $C_{1-6}$alkyl, $C_{1-4}$alkyl, methyl, ethyl, butyl), optionally substituted alkenyl (e.g., $C_{2-10}$alkenyl, $C_{2-6}$alkenyl, $C_{2-4}$alkenyl, ethenyl), optionally substituted alkynyl (e.g., $C_{2-10}$alkynyl, $C_{2-6}$alkynyl, $C_{2-4}$alkynyl, ethynyl), optionally substituted aryl (e.g., $C_{6-14}$aryl, $C_{6-10}$aryl, phenyl), optionally substituted heteroaryl (e.g., heteroaryl containing 1-4 nitrogen atoms, 5-6 membered heteroaryl, thienyl), or an electron donating group. In certain embodiments, $R^1$ and $R^2$ are independently optionally substituted alkyl, optionally substituted aryl, optionally substituted heteroaryl, or an electron donating group. In some instances, $R^1$ and $R^2$ are independently optionally substituted alkyl, optionally substituted aryl, or an electron donating group. For instance, $R^1$ and $R^2$ may be independently optionally substituted alkyl or an electron donating group.

In certain embodiments, $R^1$ and $R^2$ are independently hydrogen, optionally substituted alkyl, or an electron donating group. In some such cases, $R^1$ and $R^2$ are independently optionally hydrogen, substituted $C_{1-6}$alkyl, or an electron donating group. In some instances, $R^1$ and $R^2$ are independently optionally substituted alkyl or an electron donating group. For instance, $R^1$ and $R^2$ may be independently optionally substituted $C_{1-6}$alkyl or an electron donating group. In some cases, $R^1$ or $R^2$ is hydrogen or optionally substituted alkyl. In other cases, $R^1$ or $R^2$ is optionally substituted alkyl (e.g., $C_{1-6}$alkyl).

In some embodiments, the electron donating group is —$(R^6)_n$—$R^7$, wherein:

each $R^6$ is independently optionally substituted alkylene, optionally substituted alkenylene, optionally substituted alkynylene, optionally substituted arylene, optionally substituted heteroalkylene, optionally substituted heteroalkenylene, optionally substituted heteroalkynylene, or optionally substituted heteroarylene;

$R^7$ is optionally substituted amino, optionally substituted thiol, or optionally substituted hydroxyl; and n is 1-5.

In some embodiments, each $R^6$ is independently optionally substituted alkenylene, optionally substituted alkynylene, optionally substituted arylene, optionally substituted heteroalkylene, optionally substituted heteroalkenylene, optionally substituted heteroalkynylene, or substituted heteroarylene. In some instances, each $R^6$ is independently optionally substituted alkenylene, optionally substituted alkynylene, optionally substituted arylene, or optionally substituted heteroarylene (e.g., furanyl, thienyl, triazole, pyrazolyl, imidazolyl, pyrrolyl). For instance, each $R^6$ may be independently —C(R)=C(R)—, —C≡C—, phenylene, or optionally substituted 5-6 membered heteroarylene, wherein R is hydrogen or optionally substituted alkyl(e.g., $C_{1-6}$alkyl).

In certain embodiments, each $R^6$ is independently optionally substituted alkenylene, optionally substituted alkynylene, or optionally substituted arylene. In some such embodiments, each $R^6$ is —C(R)=C(R)—, —C≡C—, or optionally substituted arylene, wherein R is hydrogen or optionally substituted alkyl(e.g., $C_{1-6}$alkyl). In some embodiments, each $R^6$ is independently optionally substituted alkenylene (e.g., $C_{2-6}$alkenylene) or optionally substituted arylene.

In some embodiments, at least one $R^6$ is optionally substituted alkenylene, optionally substituted arylene, or optionally substituted heteroarylene. In some such embodiments, each $R^6$ is —C(R)=C(R)—, optionally substituted arylene, or optionally substituted heteroarylene, wherein R is hydrogen or optionally substituted alkyl (e.g., $C_{1-6}$alkyl). In some embodiments, each $R^6$ is independently optionally substituted alkenylene (e.g., $C_{2-6}$alkenylene) or optionally substituted heteroarylene.

In some embodiments, the electron donating group is -alkenylene-arylene-arylene-$R^7$, -alkenylene-arylene-heteroarylene-$R^7$, -alkenylene-heteroarylene-arylene-$R^7$, -alkenylene-heteroarylene-heteroarylene-$R^7$, -alkynylene-arylene-arylene-$R^7$, -alkynylene-arylene-heteroarylene-$R^7$, -alkynylene-heteroarylene-arylene-$R^7$, -alkynylene-heteroarylene-heteroarylene-$R^7$,-alkenylene-arylene-$R^7$, -alkenylene-heteroarylene-$R^7$, -alkynylene-arylene-$R^7$, -alkynylene-heteroarylene-$R^7$, -alkenylene-$R^7$, -heteroarylene-$R^7$, -alkynylene-$R^7$, or arylene-$R^7$, each of which may be optionally substituted. In some instances, the electron donating group is -alkenylene-arylene-arylene-$R^7$, -alkenylene-arylene-heteroarylene-$R^7$, -alkenylene-heteroarylene-arylene-$R^7$, -alkenylene-heteroarylene-heteroarylene-$R^7$, -alkenylene-arylene-$R^7$, -alkenylene-arylene-alkenylene-arylene-$R^7$, or -alkenylene-heteroarylene-$R^7$, each of which may be optionally substituted. In certain embodiments, the electron donating group is —C(R)=C(R)-arylene-arylene-$R^7$, —C(R)=C(R)-arylene-heteroarylene-$R^7$, —C(R)=C(R)-heteroarylene-arylene-$R^7$, —C(R)=C(R)-heteroarylene-heteroarylene-$R^7$, —C(R)=C(R)-arylene-$R^7$, —C(R)=C(R)-heteroarylene-$R^7$, —C(R)=C(R)-arylene-C(R)=C(R)-arylene—$R^7$, -arylene-arylene-$R^7$, —C≡C-arylene-heteroarylene-$R^7$, —C≡C-heteroarylene-arylene-$R^7$, —C≡C-heteroarylene-heteroarylene-$R^7$, —C≡C-arylene-$R^7$, or —C≡C-heteroarylene-$R^7$. In some certain embodiments, the electron donating group is —C(R)=C(R)-arylene-arylene-$R^7$, —C(R)=C(R)-arylene-heteroarylene-$R^7$, —C(R)=C(R)-heteroarylene-arylene-$R^7$, —C(R)=C(R)-heteroarylene-heteroarylene-$R^7$, —C(R)=C(R)-arylene-$R^7$, or —C(R)=C(R)-heteroarylene-$R^7$. In some embodiments, each R is independent hydrogen or optionally substituted alkyl. In some embodiments, each R is hydrogen. In some such cases, the arylene is optionally substituted phenylene and/or the heteroarylene is optionally substituted thienyl or optionally substituted furanyl. In some such cases, each arylene is optionally substituted phenylene. In some such cases, each arylene is unsubstituted phenylene. In some embodiments $R^7$ is —N(R")$_2$ or —OR', and R' and R" are independently hydrogen or optionally substituted alkyl.

In some embodiments, $R^7$ is optionally substituted amino, optionally substituted thiol, or optionally substituted hydroxyl. For instance, $R^7$ may be —N(R")$_2$, —SR', or —OR', wherein R' and R" are independently hydrogen or optionally substituted alkyl (e.g., $C_{1-12}$alkyl, $C_{2-12}$alkyl). In certain embodiments, $R^7$ is optionally substituted amino or optionally substituted hydroxyl. In some such cases, $R^7$ is —N(R")$_2$ or —OR', and R' and R" are independently hydrogen or optionally substituted alkyl. In certain embodiments, $R^7$ is optionally substituted amino or optionally substituted thiol. In some such cases, $R^7$ is —N(R")$_2$, —SR', and R' and R" are independently hydrogen or optionally substituted alkyl (e.g., $C_{1-12}$alkyl, $C_{2-12}$alkyl). In some cases, $R^7$ is $R^7$ is —N(R")$_2$ or optionally substituted thiol, wherein each R" is independently $C_{1-12}$ alkyl, provided that at least one R" is $C_{2-12}$alkyl. In certain cases, $R^7$ is $R^7$ is —N(R")$_2$, wherein each R" is independently $C_{1-12}$ alkyl, provided that at least one R" is $C_{2-12}$alkyl. In some embodiments $R^7$ is —OR', and R' is hydrogen or optionally substituted alkyl.

In some embodiments, n is 1-4, 1-3, or 1-2. In some cases, n is 1, 2, 3, 4, or 5. In some instances, n is 1 or 2. In certain embodiments, n is 1-3.

For instance, in some embodiments for a compound of Formula I:

$R^1$ and $R^2$ are independently hydrogen, optionally substituted alkyl, or an electron donating group, provided that at least one of $R^1$ and $R^2$ is an electron donating group;

each $R^3$ is independently hydrogen, optionally substituted alkyl, halo, or a linking group;

each $R^4$ is hydrogen or optionally substituted alkyl;

Ring A is optionally substituted arylene or optionally substituted heteroarylene;

$R^5$ is optionally substituted acylene, optionally substituted alkenylene, optionally substituted alkylene, optionally substituted alkynylene, substituted amino, optionally substituted arylene, optionally substituted heteroalkenylene, optionally substituted heteroalkylene, optionally substituted heteroalkynylene, optionally substituted heteroarylene, —O—, or optionally substituted thiolene;

X is a polar group, wherein X is charged or has a log(P) of less than or equal to about 0;

the electron donating group is —(R$^6$)$_n$—R$^7$:

each $R^6$ is independently optionally substituted alkenylene, optionally substituted alkynylene, optionally substituted arylene, or optionally substituted heteroarylene;

$R^7$ is —N(R")$_2$ or optionally substituted thiol;

each R" is independently $C_{1-12}$ alkyl, provided that at least one R" is $C_{2-12}$alkyl; and n is 1-5.

In some embodiments, one or moieties at the $R^3$ position may serve to improve solubility, provide a linking group for conjugation to another molecule (e.g., biological molecule), and/or tether a biological molecule to the core of the dye. In some embodiments, each $R^3$ is independently hydrogen, optionally substituted alkyl, halo, or a linking group. In certain embodiments, each $R^3$ is independently hydrogen, optionally substituted alkyl, or halo. In certain embodiments, at least one $R^3$ is a linking group. In certain embodiments, the linking group is —(R$^{10}$)$_p$—R$^{11}$, wherein:

each $R^{10}$ is independently a charged group, optionally substituted acylene, optionally substituted alkenylene, optionally substituted alkylene, substituted amino, optionally substituted arylene, optionally substituted carbocyclylene, optionally substituted heteroalkenylene, optionally substituted heteroalkylene, optionally substituted heteroarylene, optionally substituted heterocyclylene, —O—, oxo, optionally substituted thiolene, or thiooxo;

$R^{11}$ is a functionalizable group or a biological molecule; and p is 1-20.

In some embodiments, $R^{10}$ is independently —O—, —S—, —N(R)—, —C(O)—, —C(S)—, —C(NR)—, —C(R)=C(R)—, —C(R)$_2$—, —C(R)$_2$C(R)$_2$O—, —OC(R)$_2$C(R)$_2$—, optionally substituted arylene, optionally substituted heteroarylene, or optionally substituted heterocyclylene, wherein R is independently hydrogen or optionally substituted alkyl. In certain cases, $R^{10}$ is independently —O—, —S—, —N(R)—, —C(O)—, —C(R)$_2$—, —C(R)$_2$C(R)$_2$O—, —OC(R)$_2$C(R)$_2$—, optionally substituted arylene (e.g., phenylene), optionally substituted heteroarylene (e.g., 5-10 membered heteroarylene, 5-6 membered heteroarylene, triazole), or optionally substituted heterocyclylene (e.g., 4-10 membered heterocyclylene, 4-6 membered heterocyclylene), wherein R is independently hydrogen or alkyl. In some embodiments, at least one $R^{10}$ is —CH$_2$CH$_2$O— or —OCH$_2$CH$_2$—. In certain embodiments, $R^{10}$ is independently —C(R)$_2$C(R)$_2$O—, —OC(R)$_2$C(R)$_2$—, optionally substituted arylene, optionally substituted heteroarylene. In some such embodiments, $R^{10}$ is —[—C(R)$_2$C(R)$_2$O—]$_t$—R$^{11}$, —[OC(R)$_2$C(R)$_2$—]$_t$—R$^{11}$, heteroarylene-R$^{11}$, arylene-R$^{11}$, -arylene-[C(R)$_2$C(R)$_2$O—]$_t$—R$^{11}$, arylene-[OC(R)$_2$C(R)$_2$—]$_t$—R$^{11}$, -heteroarylene-[—C(R)$_2$C(R)$_2$O—]$_t$—R$^{11}$, heteroarylene-[OC(R)$_2$C(R)$_2$—]$_t$—R$^{11}$, arylene-heteroarylene-R$^{11}$, heteroarylene-arylene-R$^{11}$, arylene-heteroarylene-[OC(R)$_2$C(R)$_2$—]$_t$—R$^{11}$, heteroarylene-arylene-[OC(R)$_2$C(R)$_2$—]$_t$—R$^{11}$,-arylene-heteroarylene-[—C(R)$_2$C(R)$_2$O—]$_t$—R$^{11}$, or heteroarylene-arylene-[—C(R)$_2$C(R)$_2$O—]$_t$—R$^{11}$, wherein t is 1-20 (e.g., 1-18, 1-16, 1-15, 1-12, 1-10, 1-8, 1-5, 2-20, 2-18, 2-16, 2-15, 2-12, 2-10, 2-8, 2-5).

In some embodiments, $R^{11}$ is a functionalizable group. As used, herein, the term "functionalizable group" refers to a group or moiety which is capable of being chemically modified (e.g., via chemical reaction with a compound comprising a functional group). In some embodiments, the functionalizable group is a group or moiety which is capable of being chemically modified with a functional group via formation of a bond (e.g., covalent bond, non-covalent bond, etc.) or interaction (e.g., chemical or biological interaction) between the functionalizable group and the functional group. In some embodiments, the functionalizable group optionally substituted acyl, optionally substituted alkenyl, substituted amino, optionally substituted heteroalkenyl, optionally substituted heteroalkyl, optionally substituted heterocyclyl, hydroxyl, or optionally substituted thiol. For example, the functionalizable group may include a maleimide group, which is commonly used to react with thiol groups on molecules that one may want to covalently attach to the dye. Functionalizable groups will be selected readily, by those of ordinary skill in the art, based upon the description provided herein and knowledge in the art. In some embodiments, the functionalizable group is a group or moiety which is capable of being chemically modified with a functional group via formation of a covalent bond. For instance, in certain embodiments, the chemical reaction may be a coupling reaction or a substitution reaction. Those of ordinary skill in the art will be aware of suitable chemical reactions between a functionalizable group and the functional group. Non-limiting examples of chemical reactions include addition reactions (including cycloaddition), oxidation reactions, reduction reactions, elimination reactions, substitution reactions, rearrangement reactions, polymerization reactions, transition-metal catalyzed coupling or cross-coupling reactions, and olefin metathesis. It should be understood that covalent bonds may be formed by other types of reactions, as known to those of ordinary skill in the art, using functionalizable groups described herein.

In some embodiments, the functionalizable group is a group or moiety which is capable of being chemically modified with a functional group via formation of a non-covalent bond (e.g., via hydrogen-bonds, ionic bonds, dative bonds, Van der Waals interactions, or the like). In some embodiments, the functionalizable group may form a hydrogen-bond with another molecule. Functionalizable groups capable of forming hydrogen-bonds include hydrogen-bond donors and acceptors. Those of ordinary skill in the art will be able to identify hydrogen-bond donors and acceptors suitable for use in the present invention. For example, a hydrogen-bond donor may comprise at least one hydrogen atom capable of associating with a pair of electrons on a hydrogen-bond acceptor to form the hydrogen bond. In some cases, the functionalizable groups may comprise one or more hydrogen-bond donor/acceptor moieties. Other examples of functionalizable groups which may form hydrogen bonds include carbonyl groups, amines, hydroxyls, and the like.

In some cases, the functionalizable groups may comprise an electron-rich or electron-poor moiety, wherein functionalizing the functionalizable group may comprise forming an electrostatic interaction with another molecule.

In some embodiments, the functionalizable group is a group or moiety which is capable of being functionalized via a biological binding event (e.g., between complementary pairs of biological molecules). For example, a functionalizable group may comprise an entity such as biotin that specifically binds to a complementary entity, such as avidin or streptavidin, on another molecule. Biological interactions for use in the embodiments described herein can be selected readily, by those of ordinary skill in the art, based upon the description herein as their function, examples of such biological interactions, and knowledge herein and in the art as to simple techniques for identifying suitable chemical interactions.

In some embodiments, the functionalizable group may be modified to attach a biological molecule or other beneficial molecule.

In some embodiments, $R^{11}$ is a biological molecule. As used herein, the term "biological molecules" has its ordinary meaning in the arts and may refer to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant techniques) that are commonly found in nature (e.g., organisms, tissues, cells, or viruses). Specific classes of biomolecules include, but are not limited to, peptides and carbohydrates such as polysaccharides and modified polysaccharides. A particular example is the polypeptide cyclic RGD, which is a polypeptide that recognizes and binds to certain cell-surface receptors called integrins. In some embodiments, the biological molecule is a peptide or a carbohydrate. It should be understood that the biological molecule may be modified to allow for attachment. For instance, the biological molecule may be substituted (e.g., at least one hydrogen present on a group is replaced with a permissible substituent) with $R^{10}$.

In some embodiments, the biological molecule is a targeting moiety (e.g., cell surface targeting moiety). Any targeting moiety known in the art may be used. A variety of targeting moieties that molecules to particular cells are known in the art (see, for example, Cotten et al. Methods Enzym. 217:618, 1993; incorporated herein by reference). Classes of targeting moieties useful in the inventive particles include proteins, peptides, polynucleotides, small organic molecules, metals, metal complexes, carbohydrates, lipids, etc. In certain embodiments, the targeting moiety is a protein or peptide. Antibodies (e.g., humanized monoclonal antibody) or antibody fragment (e.g., Fab fragment) may be used as targeting moieties. In certain embodiments, a protein receptor or a portion of a protein receptor is used as the targeting moiety. In other embodiments, a peptide ligand (e.g. peptide hormone, signaling peptide, peptide ligand, etc.) is used as the targeting moiety. In certain particular embodiments, the targeting moiety is an RGD integrin-binding peptide. In certain embodiments, the targeting moiety is S4 domain of the C. intestinalis phosphatase enzyme. In certain embodiments, the targeting moiety is 10-mer of plannexin. In certain embodiments, the targeting moiety is a glycopeptide or glycoprotein. In certain embodiments, the targeting moiety is a polynucleotide. In certain embodiments, the targeting moiety is a carbohydrate. In certain embodiments, the targeting moiety is a carbohydrate ligand. In certain embodiments, the targeting moiety is a carbohydrate found on the surface of a cell.

In some embodiments, one or moieties at the $R^4$ position may serve to cause Ring A to twist out of the plane of the diaza-s-indacene structure, which is useful to prevent electronic interaction between ring A and $R^5$ and the rest of the dye molecule which might quench the dye fluorescence by energy or electron transfer. In some such embodiments, $R^4$ is optionally substituted $C_{1-10}$alkyl (e.g., $C_{1-6}$alkyl, $C_{1-4}$alkyl, ethyl, methyl).

In some embodiments, Ring A is optionally substituted arylene. For instance, Ring A may be phenyl. In some embodiments, Ring A is optionally substituted heteroarylene.

In some embodiments, $R^5$ is optionally substituted acylene, optionally substituted alkenylene, optionally substituted alkynylene, substituted amino, optionally substituted arylene, optionally substituted heteroalkenylene, optionally substituted heteroalkylene, optionally substituted heteroalkynylene, optionally substituted heteroarylene, —O—, or optionally substituted thiolene. In certain embodiments, $R^5$ is —C(O)—, —C(O)O—, —OC(O)—, —C(O)N(R)—, —N(R)C(O)—, —O—, —S—, —N(R)—, —C(R)$_2$—, —C≡C—, —C(R)=C(R)—, optionally substituted arylene, or optionally substituted heteroarylene (e.g., triazole), wherein R is hydrogen or optionally substituted alkyl.

In some embodiments, X may serve to allow the voltage sensitive dye to have a beneficial association with and/or orientation at or in the cell membrane, provide a linking group for conjugation to another molecule (e.g., biological molecule), and/or tether a biological molecule to the core of the dye. For instance, in some embodiments, X may contain a polar group, such as an ionically charged group (e.g., one or more quaternary ammonium salts) or a polyethylene glycol oligomer. Without being bound by theory, it is believed that polar groups will tend to stay in the polar extracellular region when the dye is applied to cells, while the nonpolar part of the dye inserts into the cell plasma membrane. In such embodiments, the dye will tend to be oriented with its longer axis perpendicular to the cell membrane. This orientation may facilitate interaction of the difference dipole moment of the dye and the electric field across the cell membrane and hence voltage sensing. In certain embodiments, X would not serve this purpose if positioned elsewhere on the diaza-s-indacene structure.

In some embodiments, X is a polar group. In certain embodiments, X is a polar group, wherein X comprises a positively charged moiety, provided that the positively charged moiety is not a metal. Regardless of whether X comprises a positively charged moiety, the polar group may be a hydrophilic group or a linking group. In certain embodiments, X is a polar group, wherein X comprises a negatively charged moiety or a precursor thereof. In some embodiments, X comprises a polar group that is hydrophilic.

In certain embodiments, the hydrophilic group (e.g., X) is —$(R^8)_m$—$R^9$, wherein:

each $R^8$ is independently a charged group, optionally substituted acyl, optionally substituted alkenylene, optionally substituted alkylene, substituted amino, optionally substituted arylene, optionally substituted carbocyclylene, optionally substituted heteroalkenylene, optionally substituted heteroalkylene, optionally substituted heteroarylene, optionally substituted heterocyclylene, —O—, oxo, optionally substituted thiolene, thiooxo, or optionally substituted siloxylene;

$R^9$ is hydrogen, a charged group, optionally substituted acyl, optionally substituted alkyl, optionally substituted amino, optionally substituted aryl, optionally substituted carbocyclyl, optionally substituted heteroalkyl, optionally substituted heteroaryl, optionally substituted heterocyclyl, optionally substituted hydroxyl, nitrile, optionally substituted siloxy, or optionally substituted thiol; and m is 0-20.

In certain embodiments, the hydrophilic group is —$(R^8)_m$—$R^9$, wherein:

each $R^8$ is independently a charged group, —COOH, —COO$^-$, optionally substituted acyl, optionally substituted alkenylene, optionally substituted alkylene, substituted amino, optionally substituted arylene, optionally substituted carbocyclylene, optionally substituted heteroalkenylene, optionally substituted heteroalkylene, optionally substituted heteroarylene, optionally substituted heterocyclylene, —O—, oxo, optionally substituted thiolene, thiooxo, or optionally substituted siloxylene;

$R^9$ is hydrogen, a charged group, optionally substituted acyl, optionally substituted alkyl, optionally substituted amino, optionally substituted aryl, optionally substituted carbocyclyl, optionally substituted heteroalkyl, optionally substituted heteroaryl, optionally substituted heterocyclyl, optionally substituted hydroxyl, nitrile, optionally substituted siloxy, or optionally substituted thiol; and m is 0-20.

In certain embodiments $R^8$ and $R^9$ are independently optionally substituted with one or more one or more hydrogen-bond donor and/or acceptor groups (e.g., acyl, amino, hydroxyl, carboxylic acid). In some embodiments, —$(R^8)_m$—$R^9$, is —COOH.

In some embodiments, each $R^8$ is independently a charged group, optionally substituted acyl, optionally substituted alkylene, substituted amino, optionally substituted arylene, optionally substituted heteroalkylene, optionally substituted heteroarylene, optionally substituted heterocyclylene, —O—, oxo, optionally substituted thiolene, thiooxo, or optionally substituted siloxylene. In certain embodiments, each $R^8$ is independently —O—, —S—, —N(R)—, —C(O)—, —C(R)$_2$—, —C(R)$_2$C(R)$_2$O—, —OC(R)$_2$C(R)$_2$—, —OSi(R)$_2$— optionally substituted arylene (e.g., phenylene), optionally substituted heteroarylene (e.g., 5-10 membered heteroarylene), optionally substituted heterocyclylene (4-10 membered, heterocyclylene), or a charged group, wherein R is independently hydrogen or alkyl.

In some embodiments, at least one $R^8$ is a charged group. In some such embodiments, each charged group is independently —N(R*)$_2$—, —P(R*)$_2$—, —S(R*)— or

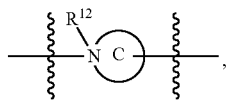

wherein:
R* is hydrogen, optionally substituted alkyl, or optionally substituted aryl; and Ring C is an optionally substituted heterocyclylene or heteroarylene ring containing at least one nitrogen atom; and each $R^{12}$ is independently absent, hydrogen or optionally substituted alkyl.

In certain embodiments, Ring C is has the structure:

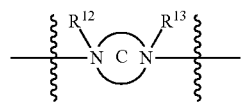

wherein Ring C is an optionally substituted heterocyclylene or heteroarylene ring containing at least two nitrogen atom and $R^{13}$ is absent, hydrogen, or optionally substituted alkyl.

In certain embodiments, Ring C is 1,4-diazabicyclo[2.2.2]octanylene.

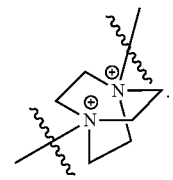 [SMILES: *[N+]12CC[N+](*)(CC1)CC2]

In some such cases, Ring C is optionally substituted

As used herein, the term "charged group" has its ordinary meaning in the art and may refer to a group comprising one or more charged moiety. As used herein, a "charged moiety" is a chemical moiety that carries a formal electronic charge, e.g., monovalent (+1), divalent (+2), trivalent (+3), etc. The charged moiety may be anionic (i.e., negatively charged) or cationic (i.e., positively charged). Examples of negatively-charged groups or precursors thereof, include carboxylate groups, sulfonate group, sulfate groups, phosphonate groups, phosphate groups, hydroxyl groups, and the like. Examples of positively-charged moieties include amino groups (e.g., protonated primary, secondary, and/or tertiary nitrogen atoms), quaternary ammonium groups, quaternary phosphonium groups, pyridinium group, and imidizolium groups. In a particular embodiment, the charged moieties comprise quaternary ammonium groups and/or quaternary phosphonium groups. In some cases, one or more charged moieties are positively charged. In certain case, all of the charged moieties are positively charged. The charge of the charged moiety may vary, in some cases, with the environmental conditions, for example, changes in pH may alter the charge of the moiety, and/or cause the moiety to become charged or uncharged. Typically, the charge of a moiety is determined under environmental conditions at which the dye is used. In general, the charge density of the dye may be selected as desired. In some embodiments, the charged moiety is not a metal (e.g., copper).

Typically associated with the charged moiety are one or more counterions, such that the charged moiety and the counterions together are electroneutral (i.e., have a zero net electronic charge). Thus, positively charged moieties may be associated with an anionic charged moieties (e.g., anionic counterion), while negatively charged moieties (for example, carboxylates, sulfonates, etc.) may be associated with a cationic charged moieties (e.g., cationic counterion).

The counterion may be any suitably charged moiety, atomic or molecular, that can associate with the charged moiety of the dye. The counterions can be loosely associated with the charged moiety in some instances, i.e., the counterions can be exchanged under ambient conditions with the same or different ions (e.g., $Li^+$ may be exchangeable for $Li^+$ or $Na^+$, etc.).

A cationic counterion may be associated with a negatively charged moiety. For example, if the charged moiety has a $-1$ charge, the counterions may be any ions having a $+1$ charge, for example, alkali metals such as $Na^+$, $Li^+$, $K^+$, etc., and/or other $+1$ charged species, such as $Cu^+$, $NH_4^+$, etc. Similarly, if the charged moiety has a $-2$ charge, the counterions may be any ions having a $+2$ charge, for example $Ca^{2+}$, $Be^{2+}$, $Fe^{2+}$, $Mg^{2+}$, $Cu^{2+}$, $Ni^{2+}$, $Sn^{2+}$, $Zn^{2+}$, $2Na^+$, $2Li^+$, $2K^+$, $Li^+$ and $Na^+$, $Li^+$ and $K^+$, $Na^+$ and $K^+$, etc. More than one counterion may be present in some cases.

An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, and the like), $BF_4^-$, $PF_4^-$, $PF_6^-$, $SbF_6^-$, $B[3,5-(CF_3)_2C_6H_3]_4]^-$, $BPh_4^-$, $Al(OC(CF_3)_3)_4$, and a carborane anion (e.g., $CB_{11}H_{12}^-$ or $(HCB_{11}Me_5Br_6)^-$).

In some embodiments, $R^9$ is a charged group. In some embodiments, the charged group is a quaternary ammonium or a quaternary phosphonium. In certain embodiments, the charged group is independently $-N(R^*)_3$, $-P(R^*)_3$, $-S(R^*)_2$, or

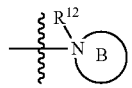

wherein:
R* is hydrogen, optionally substituted alkyl, or optionally substituted aryl; and
Ring B is an optionally substituted heterocyclic or heteroaryl ring containing at least one nitrogen atom; and $R^{12}$ is absent, hydrogen, or optionally substituted alkyl. In some cases, the charged group is independently $-N(R^*)_3$ or

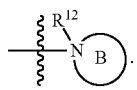

In some such embodiments, Ring B is pyridinyl, maleimidyl, or succinimidyl. In certain embodiments, Ring B has the structure:

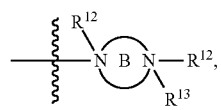

wherein Ring B is an optionally substituted heterocyclic or heteroaryl ring containing at least two nitrogen atom and $R^{13}$ is absent, hydrogen, or optionally substituted alkyl. In certain embodiments, Ring B is 1,4-diazabicyclo[2.2.2]octanyl. In some such cases, Ring B is optionally substituted

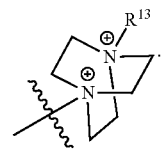

In other embodiments, $R^9$ is hydrogen or optionally substituted alkyl.

In some embodiments, X is a linking group as described herein. In some such embodiments, X is $-(R^{10})_p-R^{11}$. In certain embodiments, $R^{10}$, $R^{11}$, and p may be defined as described above. In some embodiments, $R^{10}$ is a charged group as described herein.

Regardless of whether X is a hydrophilic group or a linking group, X may be charged and/or have a log(P) of less than or equal to about 0. In some embodiments, X may be charged. In certain embodiments, X may have a formal charge between $-10$ to $+10$ (e.g., $-6$ to $+6$, $-3$ to $+6$, $-1$ to $+6$, $+1$ to $+6$). In some instances, X may have a formal charge between $+1$ and about $+10$. In some such embodiments, X may have a formal charge of $+1$, $+2$, $+3$, $+4$, $+5$, or $+6$. In some embodiments, X may be zwitterionic. In certain embodiments, X may be cationic (e.g., diacationic).

In certain embodiments, X may be anionic (e.g., dianionic). As noted above, non-limiting examples of anionic (e.g., negatively-charged) groups or precursors thereof, include carboxylate groups, sulfonate group, sulfate groups, phosphonate groups, phosphate groups, hydroxyl groups, and the like. In some embodiments, X is $-COOH$, which may form $-COO^-$ depending on the conditions (e.g., in basic conditions). In some embodiments, X is $-COO^-$. In some embodiments, for a compound of formula (I), Ring A is optionally substituted arylene or optionally substituted heteroarylene; $R^5$ is optionally substituted acylene, optionally substituted alkenylene, optionally substituted alkylene, optionally substituted alkynylene, substituted amino, optionally substituted arylene, optionally substituted heteroalkenylene, optionally substituted heteroalkylene, optionally substituted heteroalkynylene, optionally substituted heteroarylene, $-O-$, or optionally substituted thiolene; and X is a negatively-charge group or a precursor thereof. In some embodiments, Ring A is optionally substituted arylene, $R^5$ is optionally substituted alkenylene, and X is $-COOH$ or $-COO^-$. In some embodiments $R^5$ is substituted with a negatively-charged group, such that $R^5-X$ comprises two negatively charged groups. For example, $R^5$ may be substituted with $-COOH$ or $-COO^-$ and X may be $-COOH$ or $-COO^-$. In some embodiments, for a compound of Formula (I), $-R^5-X$ has the structure:

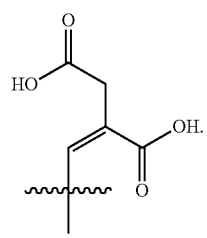

In some embodiments, for a compound of Formula (I), -(Ring A)-R⁵—X has the structure:

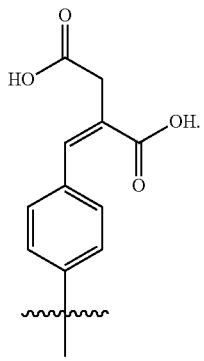 [SMILES: *c1ccc(/C(C)=C(\CC(=O)O)C(=O)O)cc1]

In some embodiments, X may have a log(P) of less than or equal to about 0 (e.g., −1). The log P value of a group, which is the logarithm of its partition coefficient between n-octanol and water, is a well-established measure of the group's hydrophilicity. Low hydrophilicities and therefore high log P values cause high absorption or permeation into cell membranes, while low values of log P lead to that moiety tending to remain in the water-rich region outside of the cell membrane. Without being bound by theory, it is believed that to have a reasonable probability of the dye not being translocated through the cell plasma membrane, the log P value should be less than or equal to about 0. Those of ordinary skill in the art would be knowledgeable of methods of determining the water-octanol partition coefficient of compounds. For example, the log P of a compound or part of a compound may be estimated using computer software.

For instance, in some embodiments, for a compound of Formula I:

$R^1$ and $R^2$ are independently hydrogen, optionally substituted alkyl, optionally substituted alkenyl, optionally substituted alkynyl, optionally substituted aryl, optionally substituted heteroaryl, or an electron donating group, provided that at least one of $R^1$ and $R^2$ is an electron donating group;

each $R^3$ is independently hydrogen, optionally substituted alkyl, halo, or a linking group;

each $R^4$ is hydrogen or optionally substituted alkyl;

Ring A is optionally substituted arylene or optionally substituted heteroarylene;

$R^5$ is optionally substituted acylene, optionally substituted alkenylene, optionally substituted alkylene, optionally substituted alkynylene, substituted amino, optionally substituted arylene, optionally substituted heteroalkenylene, optionally substituted heteroalkylene, optionally substituted heteroalkynylene, optionally substituted heteroarylene, —O—, or optionally substituted thiolene; and X is a polar group, wherein X comprises a positively charged moiety, provided that the positively charged moiety is not a metal.

For instance, in some embodiments, for a compound of Formula I:

$R^1$ and $R^2$ are independently hydrogen, optionally substituted alkyl, optionally substituted alkenyl, optionally substituted alkynyl, optionally substituted aryl, optionally substituted heteroaryl, or an electron donating group, provided that at least one of $R^1$ and $R^2$ is an electron donating group;

each $R^3$ is independently hydrogen, optionally substituted alkyl, halo, or a linking group;

each $R^4$ is hydrogen or optionally substituted alkyl;

Ring A is optionally substituted arylene or optionally substituted heteroarylene;

$R^5$ is optionally substituted acylene, optionally substituted alkenylene, optionally substituted alkylene, optionally substituted alkynylene, substituted amino, optionally substituted arylene, optionally substituted heteroalkenylene, optionally substituted heteroalkylene, optionally substituted heteroalkynylene, optionally substituted heteroarylene, —O—, or optionally substituted thiolene; and X is a polar group, wherein X comprises a negatively charged moiety.

In some embodiments, the voltage sensitive dye is:

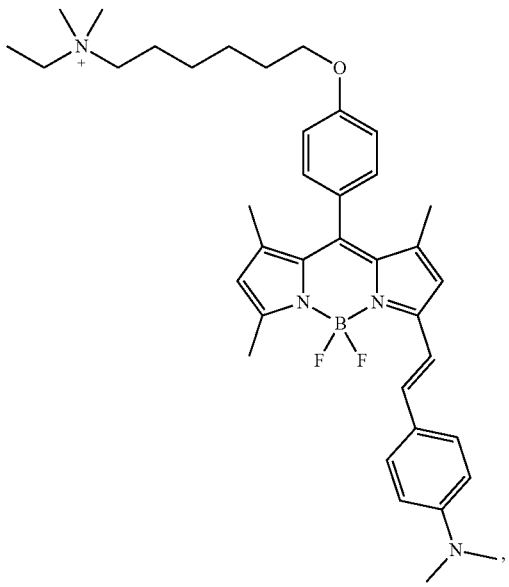

I-1

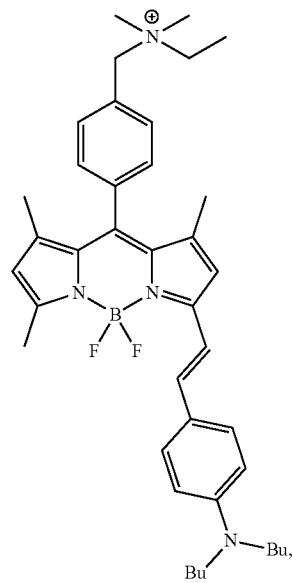

I-2

-continued
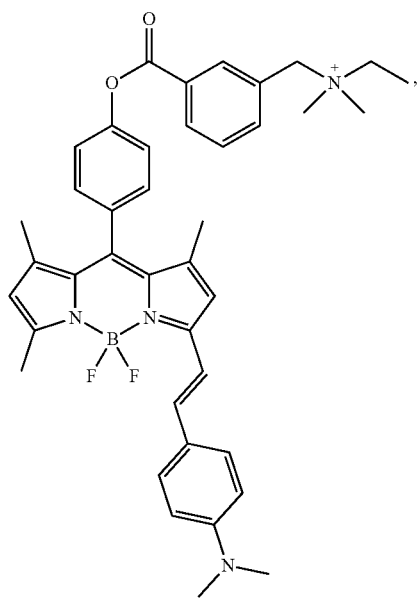
I-3
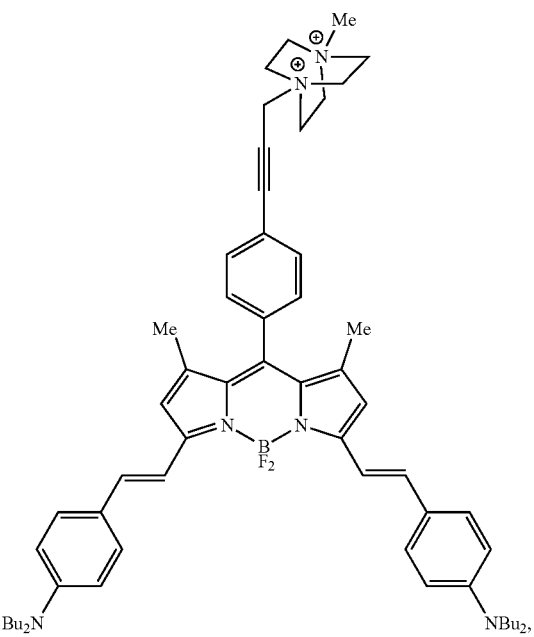
I-5
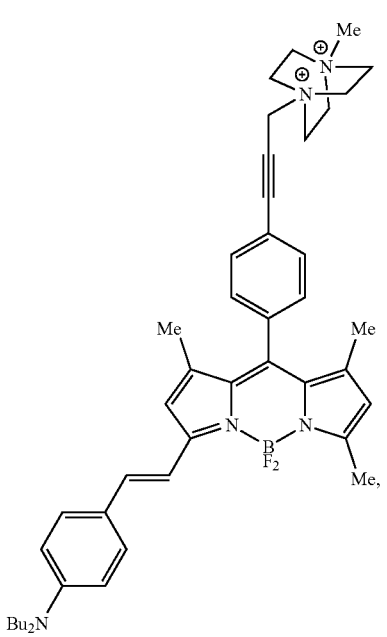
I-6
I-4
or a salt thereof.

In some embodiments, the voltage sensitive dye is:

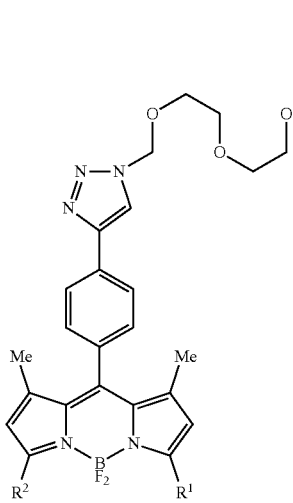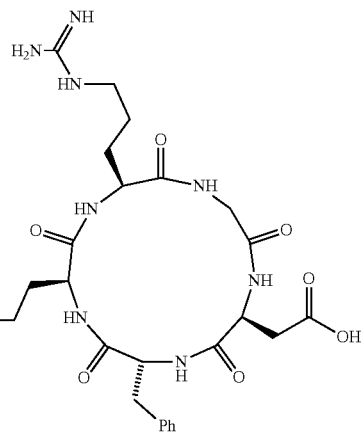

I-7 or a salt thereof, wherein $R^1$ and $R^2$ are as described herein.

In some embodiments, the voltage sensitive dye is:

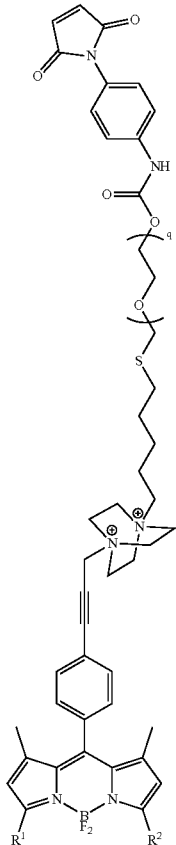

I-8 or a salt thereof, wherein q is 1 to 20 (e.g., 2 to 20, 4 to 20) and $R^1$ and $R^2$ are as described herein. In some instances, $R^1$ and $R^2$ are independently H or —CH=CH— phenylene-N$(R'')_2$.

In some embodiments, the voltage sensitive dye is:

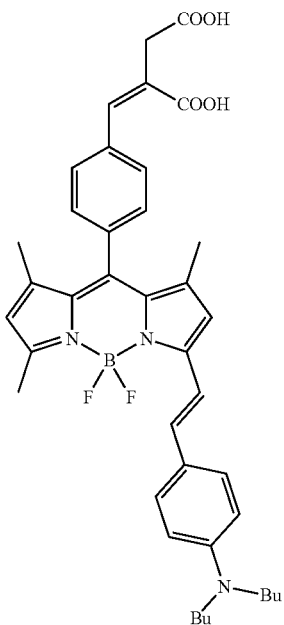

I-9 or a salt thereof.

In some embodiments, the voltage sensitive dye is:

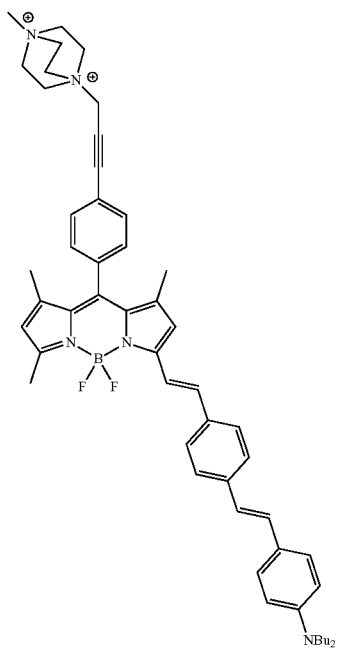

I-10 or a salt thereof.

In some embodiments, the voltage sensitive dye comprises Formula (II):

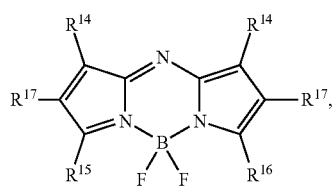

(II)

or a salt thereof, wherein:

each $R^{14}$ is optionally substituted alkyl, optionally substituted alkenyl, optionally substituted alkynyl, optionally substituted heteroalkyl, optionally substituted heteroalkenyl, optionally substituted heteroalkynyl, optionally substituted aryl, optionally substituted heteroaryl;

$R^{15}$ is optionally substituted alkyl, optionally substituted alkenyl, optionally substituted alkynyl, optionally substituted heteroalkyl, optionally substituted heteroalkenyl, optionally substituted heteroalkynyl, optionally substituted aryl, optionally substituted heteroaryl, wherein $R^{15}$ is substituted with an electron-donating group;

$R^{16}$ is optionally substituted alkyl, optionally substituted alkenyl, optionally substituted alkynyl, optionally substituted heteroalkyl, optionally substituted heteroalkenyl, optionally substituted heteroalkynyl, optionally substituted aryl, optionally substituted heteroaryl, wherein $R^{16}$ is substituted with an electron-withdrawing group; and each $R^{17}$ is independently hydrogen, optionally substituted alkyl, halo, or a linking group.

In some embodiments, each $R^{14}$ is optionally substituted aryl. In some embodiments, each $R^{14}$ is optionally substituted phenyl. In some embodiments, each $R^{14}$ is phenyl.

In some embodiments, $R^{15}$ is optionally substituted aryl. In some embodiments, $R^{15}$ is optionally substituted phenyl. In some embodiments, $R^{15}$ is phenyl substituted with $N(R^{18})_2$, wherein each $R^{18}$ is independently optionally substituted alkyl. In some embodiments, $R^{15}$ is phenyl substituted with $NMe_2$.

In some embodiments, $R^{16}$ is substituted with an electron-withdrawing group, wherein the electron-withdrawing group is a positively-charged group. In some embodiments, the positively charged group is $-N(R^{19})_3^+$, wherein each $R^{19}$ is independently optionally substituted alkyl. In some embodiments, $R^{16}$ is optionally substituted phenyl. In some embodiments, $R^{16}$ is phenyl substituted with $N(R^{19})_3^+$, wherein each $R^{19}$ is independently optionally substituted alkyl. In some embodiments, $R^{16}$ is phenyl substituted with $NMe_3^+$. As described herein, typically associated with the charged moiety are one or more counterions, such that the charged moiety and the counterions together are electroneutral (i.e., have a zero net electronic charge).

In some embodiments, each $R^{14}$ is optionally substituted aryl (e.g., substituted or unsubstituted phenyl), $R^{15}$ is phenyl substituted with $N(R^{18})_2$, wherein each $R^{18}$ is independently optionally substituted alkyl, $R^{16}$ is phenyl substituted with $N(R^{19})_3^+$, wherein each $R^{19}$ is independently optionally substituted alkyl, and each $R^{17}$ is hydrogen.

In some embodiments, the voltage sensitive dye comprising Formula (II) has the structure:

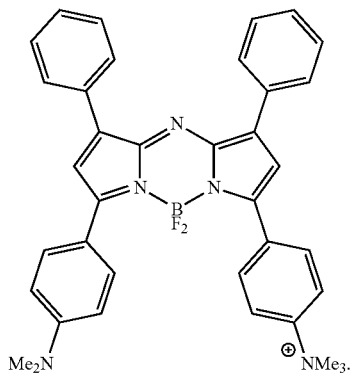

In some embodiments, the voltage sensitive dyes, described herein, may not suffer from one or more limitations of some conventional voltage sensitive dyes. For instance, in some embodiments, the voltage sensitive dye may have a relatively long emission wavelength. In some embodiments, the voltage sensitive dye may have an emission wavelength maximum of greater than or equal to about 650 nm and less than or equal to about 900 nm in toluene, dichloromethane, methanol, or dimethylsulfoxide. In some embodiments, the emission wavelength maximum may be in the near-infrared range.

In some embodiments, the voltage sensitive dye may have a relatively long absorbance wavelength. In certain embodiments, the long absorption wavelength maximum may be used to minimize autofluorescence of other materials in the cells. In some embodiments, the voltage sensitive dye may have an absorbance wavelength maximum of greater than or equal to about 600 nm and less than or equal to about 800 nm in toluene, dichloromethane, methanol, or dimethylsulfoxide. In some embodiments, the absorbance wavelength may be in the visible range. In some embodiments, the absorbance wavelength maximum may be in the near-infrared range.

In some embodiments, the voltage sensitive dye may have a relatively large Stokes shift. In some embodiments, the large Stokes shift facilitates fluorescence imaging. For instance, in some embodiments, the Stoke shift may be greater than or equal to about 20 nm, greater than or equal to about 40 nm, greater than or equal to about 60 nm, or greater than or equal to about 80 nm, consistent with the absorbance and fluorescence ranges described above.

In some embodiments, the voltage sensitive dye may have a relatively high fluorescence yield. The fluorescence yield of the dye in a nonpolar solvent (e.g., toluene or dichloromethane) may be greater than or equal to about 0.1, greater than or equal to about 0.2, greater than or equal to about 0.3, greater than or equal to about 0.4, greater than or equal to about 0.5, and less than or equal to about 1. The fluorescence yield may be measured as described in Demas & Crosby, J. Phys. Chem. 75, 991-1024 (1971).

In some embodiments, the voltage sensitive dye may have a relatively fast response speed. The response speed is the time necessary for the dye's absorbance or fluorescence to change after the membrane voltage changes. In some embodiments, the response speed is less than or equal to about 1 ms, less than or equal to about 0.5 ms, less than or equal to about 0.1 ms, less than or equal to about 0.05 ms, less than or equal to about 0.01 ms, less than or equal to about 0.005 ms, less than or equal to about 0.001 ms, or less than or equal to about 0.0005 ms, The response speed may be measured by comparing membrane voltage changes measured using the dye with voltage changes measured using implanted electrodes. In some embodiments, the dyes, described herein, may operate by an electrochromic response and have a response speed of less than or equal to about 0.001 ms.

In some embodiments, the voltage sensitive dye may have a relatively high molar absorptivity. The molar absorptivity (measured at the peak of the dye's long wavelength absorption band) is ideally over 50,000 $M^{-1}cm^{-1}$ and as much greater than this as possible. It is measured by measuring the absorbance, in a suitable solvent such as toluene or methanol, of a known concentration of dye and applying the Beer-Lambert law.

In some embodiments, the voltage sensitive dye may have a relatively high voltage sensitivity. Voltage sensitivity is generally reported as the fractional change in dye fluorescence per 100 mV change in membrane voltage, measured in a fluorescence microscope with the membrane voltage set by an electrode inserted into the cell (patch clamping). Voltage sensitivity measured and reported in this way is preferably >0.1 and more preferably >0.2, and can range up to about 0.5 with higher values preferred.

In one aspect, methods for using the voltage sensitive dyes described herein are provided. In some embodiments, the method comprises exposing a cell membrane to a voltage-sensitive dye. The voltage sensitive dye may comprise an electron acceptor comprising boron, an electron donor, and a polar group. The voltage sensitive dye may have any of the properties described herein. For instance, the voltage sensitive dye may have a maximum absorbance wavelength in methanol of the voltage-sensitive dye of greater than or equal to about 600 nm.

In some embodiments, the method also comprises allowing the voltage-sensitive dye to orient in the cell membrane such that at least a portion of the electron acceptor is positioned within the cell membrane and at least a portion of the polar group is positioned outside of the cell membrane. In certain embodiments, the dye may orient in the cell membrane without the application of energy or external stimulus. For instance, the dye may spontaneously orient due at least in part to the position and/or nature of the hydrophobic and polar groups on the dye. In some embodiments, the polar group helps to align the difference dipole moment of the dye perpendicular to the outer surface of the cell membrane.

In some embodiments, the voltage sensitive dye may be used to determine a change in a potential across the cell membrane. In some embodiments, the peak wavelength of absorption or emission may correlate with the magnitude of the potential across the cell membrane. In certain embodiments, the integrated emission of the dye (e.g., fluorescence) is measured (e.g., using a fluorescence microscope with a camera for detection and the fluorescence detected using light filters).

"Biomolecules": The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant techniques) that are commonly found in nature (e.g., organisms, tissues, cells, or viruses). Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, siRNA, DNA, and RNA.

The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least two nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, 2'-methoxyribose, 2'-aminoribose, ribose, 2% deoxyribose, arabinose, and hexose), or modified phosphate groups (e.g., phosphorothioates and 5'-N phosphoramidite linkages). Enantiomers of natural or modified nucleosides may also be used. Nucleic acids also include nucleic acid-based therapeutic agents, for example, nucleic acid ligands, siRNA, short hairpin RNA, antisense oligonucleotides, ribozymes, aptamers, and SPIEGELMERS™, oligonucleotide ligands described in Wlotzka, et al., *Proc. Natl. Acad. Sci. USA*, 2002, 99(13):8898, the entire contents of which are incorporated herein by reference.

According to the present invention, a "polypeptide", "peptide", or "protein" comprises a string of at least three amino acids linked together by peptide bonds. The terms "polypeptide", "peptide", and "protein", may be used interchangeably. Peptide may refer to an individual peptide or a collection of peptides. Inventive peptides preferably contain only natural amino acids, although non natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

The term "carbohydrate" refers to a sugar or polymer of sugars. The terms "saccharide", "polysaccharide", "carbohydrate", and "oligosaccharide", may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose. (e.g., 2'-fluororibose, deoxyribose, and hexose). Carbohydrates may exist in many different forms, for example, conformers, cyclic forms, acyclic forms, stereoisomers, tautomers, anomers, and isomers.

When the term "hydrophilic" is used with respect to a molecules and/or groups, the term has its ordinary meaning in the art and may refer to molecules and/or groups that have a tendency to interact with polar solvents, in particular with water, or with other polar groups. One of ordinary skill in the art would be able to readily select hydrophilic molecules and/or groups based on general knowledge in the art and the disclosure herein.

The term "electron acceptor" has its ordinary meaning in the art and may refer to a moiety that accepts an electron from another moiety.

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of a carbon by a $^{13}$C- or $^{14}$C-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and for 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and for 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C4), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and for 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

"Carbocyclyl," "carbocycle," or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (Cm), and the like. As the foregoing examples illustrate, in certain embodiments, the carbocyclyl group is either monocyclic ("monocyclic carbocyclyl") or contain a fused, bridged. or Spiro ring system such as a bicyclic system ("bicyclic carbocyclyl"). Carbocyclyl can be saturated, and saturated carbocyclyl is referred to as "cycloalkyl." In some embodiments, carbocyclyl is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl. Carbocyclyl can be partially unsaturated. Carbocyclyl including one or more C=C double bonds in the carbocyclic ring is referred to as "cycloalkenyl." Carbocyclyl including one or more C≡C triple bonds in the carbocyclic ring is referred to as "cycloalkynyl." Carbocyclyl includes aryl. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur. Exemplary 3-membered heterocyclyl groups containing 1 heteroatom include, without limitation, azirdinyl, oxiranyl, and thiiranyl.

Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl.

Exemplary 5-membered heterocyclyl groups containing 3 heteroatoms include, without limitation, triazolinyl, oxadiazolinyl, and thiadiazolinyl.

Exemplary 6-membered heterocyclyl groups containing 1 heteroatom include, without limitation, piperidinyl, tetrahydropyranyl, dihydropyridinyl, and thianyl.

Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl.

Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

As used herein, "heteroaryl" refers to a radical of a 5-14 membered monocyclic or polycyclic (e.g., bicyclic, tricyclic) 4n+2 aromatic ring system (e.g., having 6,10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl.

Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively.

Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, heteroarylene is the divalent moiety of heteroaryl, and —O— or substituted hydroxyl is the divalent moiety of hydroxyl. In some instances, a substituted amino may be divalent.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction.

Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{aa}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{aa}$)$_2$, —NR$^{bb}$P(=O)(NR$^{bb}$)$_2$, P(R$^{cc}$)$_2$, —P(R$^{cc}$)$_3$, —OP(R$^{aa}$)$_2$, —OP(R$^{aa}$)$_3$, —B(R$^{aa}$)$_2$, —B(OR$^{cc}$)$_2$, —BR$^{aa}$(OR$^{bb}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; P each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alky))$_2$, —N(C$_{1-6}$ alkyl)$_3$+X$^-$, —NH(C$_{1-6}$ alkyl)$_2$+X$^-$, —NH$_2$(C$_{1-6}$ alkyl)+X$^-$, —NH$_3$+X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C1-6 alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alky))$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

As used herein, the term "halo" or "halogen" refers to fluorine (fluoro, —F), chlorine (chloro, —Cl), bromine (bromo, —Br), or iodine (iodo, —I).

As used herein, the term "hydroxyl" or "hydroxy" refers to the group —OH. The term "substituted hydroxyl" or "substituted hydroxyl" refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, OC(=NR$^{bb}$)OR$^{aa}$, —OC(=NR$^{bb}$)N(R$^{bb}$)$_2$, —S(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term, "amino" refers to the group —NH$_2$. The term "substituted amino," by extension, refers to a monosubstituted amino, a disubstituted amino, or a trisubstituted amino, as defined herein. In certain embodiments, the "substituted amino" is a monosubstituted amino or a disubstituted amino group.

As used herein, the term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

As used herein, the term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$+ X$^-$, wherein R$^{bb}$ and X$^-$ are as defined herein.

As used herein, the term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$), —C(=NR$^{bb}$)N(R$_{bb}$)$_2$, wherein R$^{aa}$ and R$^{bb}$ are as defined herein.

As used herein, the term "silyl" refers to the group —Si(R$^{aa}$)$_3$, wherein R$^{aa}$ is as defined herein. Accordingly, the term "siloxy" refers to the group —OSi(R$^{aa}$)$_3$, wherein R$^{aa}$ is as defined herein.

As used herein, the term "oxo" refers to the group =O, and the term "thiooxo" refers to the group =S.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups.

These and other exemplary substituents are described in more detail in the Detailed Description, Examples, and claims. The invention is not intended to be limited in any manner by the above exemplary listing of substituents.

As used herein, the term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

As used herein, the term "tautomer" refers to particular isomers of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridone-hydroxypyridine forms.

The following examples are intended to illustrate certain embodiments of the present invention, but do not exemplify the full scope of the invention.

Example 1

This example describes the synthesis of I-1. The synthesis is shown in Scheme 1.

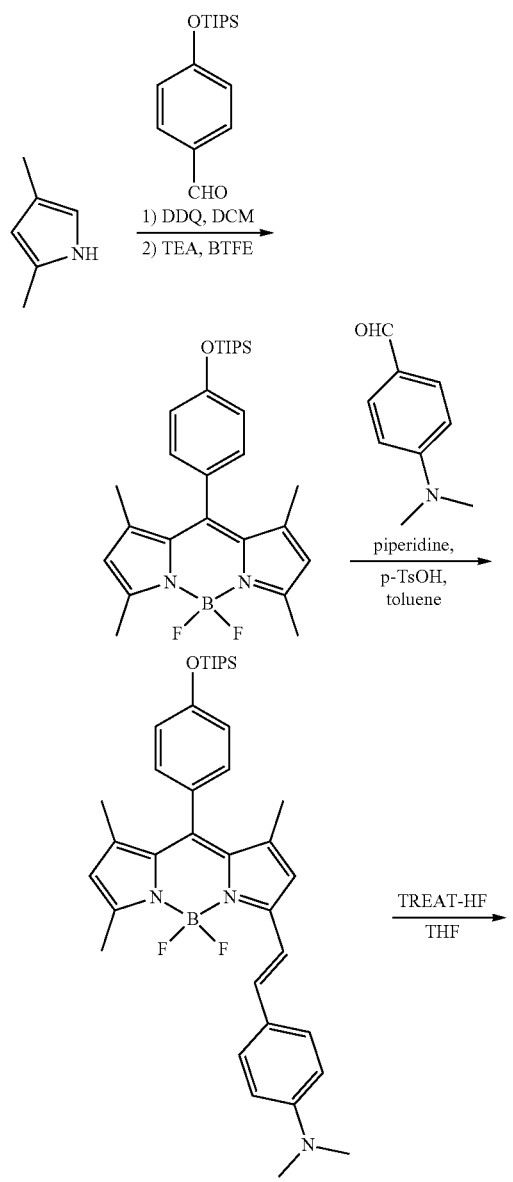

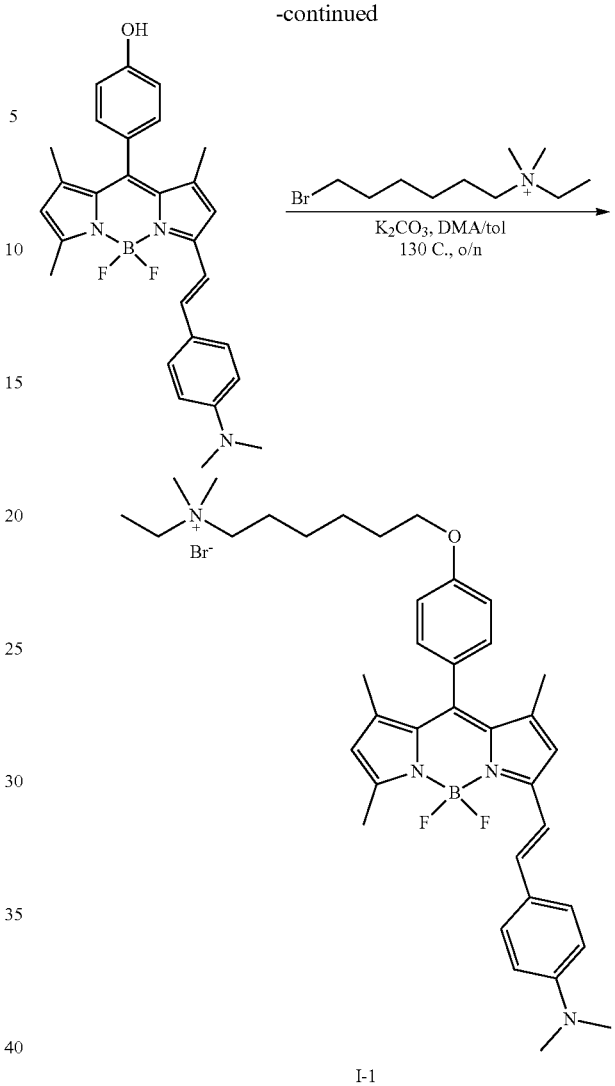

2,4-Dimethylpyrrole (MW 95.15; 1.85 g; d 0.924; 19 mmol; 2 eq; 2 mL) and 4-tri(isopropyl)silylether benzaldehyde (MW 278.46; 2.7 g; 9.7 mmol; 1 eq) were dissolved in 100 mL dichloromethane under Argon atmosphere. Two drops of TFA were added and the solution stirred at room temperature overnight. Following overnight, DDQ (MW 227.01; 2.2 g; 9.7 mmol; 1 eq) was added and stirring was continued for another 75 min. Under argon sparge, 51rimethylamine (MW 101.19; 4.9 g; d 0.726; 49 mmol; 5 eq; 6.8 mL) and boron trifluoride diethyl etherate solution (MW 141.93; 9.6 g; d 1.13; 68 mmol; 7 eq; 8.5 mL) were added and the reaction mixture was allowed to stir at room temperature. After stirring for 120 min, the reaction mixture was neutralized with a minimum volume of sodium bicarbonate solution, dried over sodium sulfate and evaporated to dryness. The residue was chromatographed on silica gel, eluting the expected product with 7/1 hexanes/ethyl acetate. The BP dye was synthesized as expected in moderate yield (22%; 1 g).

BP dye (MW 496.52; 375 mg; 0.76 mmol; 1 eq), N,N-dimethylaminobenzaldehyde (MW 149.19; 113 mg; 0.76 mmol; 1 eq), piperidine (500 uL) and p-TsOH (several crystals) were dissolved in toluene (15 mL) along with several 4 A molecular sieves. The reaction flask was fitted with multiple condensers. The reaction temperature was raised to 130° C. and the reaction mixture was allowed to reflux overnight. Following overnight, the reaction mixture was allowed to cool to room temperature. The crude material was washed into a 250 mL RB flask and then adsorbed onto silica gel. After thoroughly drying the adsorbed material, it was purified via silica gel chromatography eluting the desired mono-coupled product with 10% ethyl acetate.

TiPS-protected BP (MW 627.69; 208 mg; 0.33 mmol; 1 eq) was dissolved in 40 mL THF and stirred. To this solution was added dropwise TREAT-HF (MW 161.21; 336 mg; d 0.99; 20 eq; 334 uL). The deep blue solution was stirred at room temperature and monitored via TLC (4/1 hexane/ethyl acetate) for completeness. Reaction mixture was adsorbed directly onto silica gel and purified via FCC on CF Rf+ system, eluting the pure product with 1/1 (hexane/ethyl acetate).

BP (MW 471.35; 9 mg; 2 umol; 1 eq) and potassium carbonate (MW 138.99; 8 mg; 6 umol; 3 eq) were stirred together in toluene (3 mL) for 15 min, the 6-bromohexyl-1-(N-ethyl-N,N-dimethyl)ammonium bromide (MW 237.20; 50 mg; 0.2 mmol; 10 eq) was added and all reagents were stirred in a 2/1 toluene/dimethylacetamide (5 mL) solution at 130 C overnight. Reaction mixture was allowed to cool to room temperature and solvents were removed under reduced pressure. Crude product was dissolved in 1 mL acetonitrile and then precipitated with MTBE. Precipitate was collected, analyzed by UV-vis and fluorescence emission spectroscopy.

Example 2

This example describes the synthesis of 1-2. The synthesis is shown in Scheme 2.

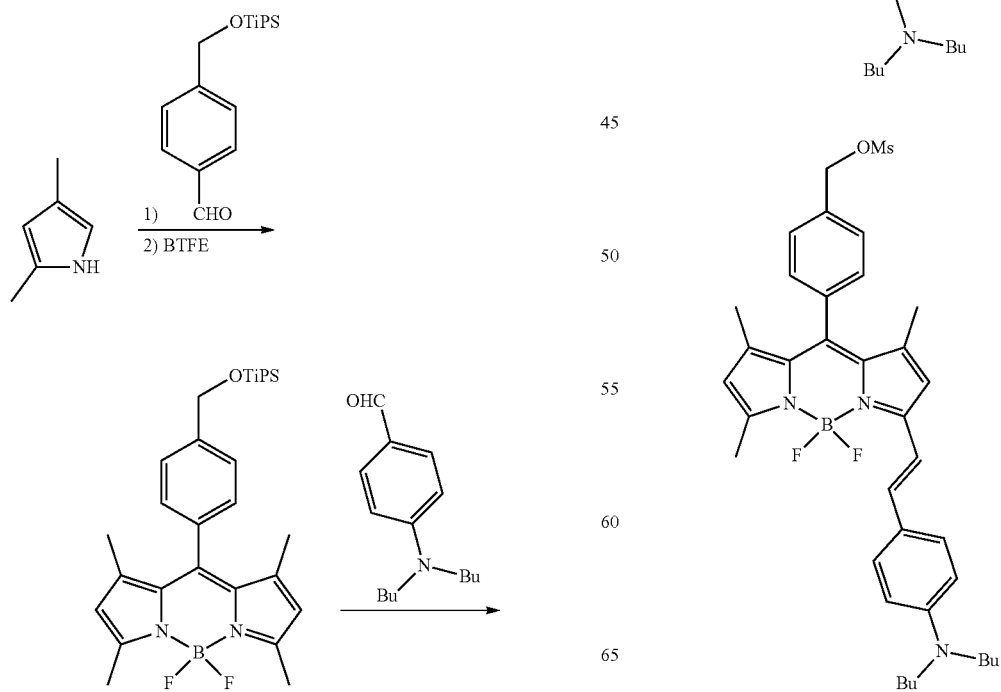

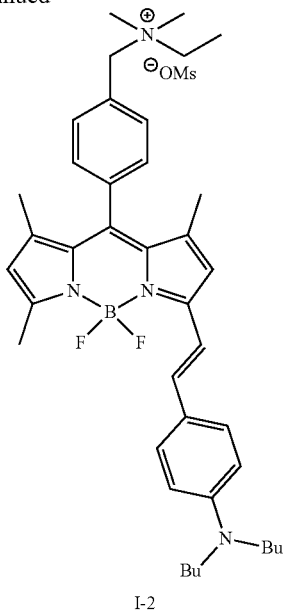

I-2

4-Hydroxymethylbenzaldehyde: To a suspension of terephthalaldehyde (MW 134.13; 14.92 mmol; 2.00 g; 1 eq) in anhydrous ethanol (50 mL) in a 250 mL Erlenmeyer flask (equipped with a magnetic stir bar) cooled to 0° C. in an ice bath, powdered sodium borohydride (MW 37.83; 5.22 mmol; 0.200 g; 0.33 eq) was added in one portion, and the reaction continued to stir at 0° C. The suspension quickly became a light yellow solution in the first minute the sodium borohydride was added. A rubber septum was used to seal the flask, and the reaction was allowed to stir for one hour. The reaction was followed by TLC with 1:1 ethyl acetate and hexanes as the eluent. At the end of the experiment, the reaction was warmed to room temperature and deionized water was added. Ethyl acetate was added to this mixture, and it was vigorously shaken. The aqueous and organic layers were separated and the aqueous layer was extracted 3×20 mL with ethyl acetate. The combined organic layers were dried with sodium sulfate and dried under reduced pressure. When the crude residue was dissolved in dichloromethane, white crystals began to form in the reaction. The flask was cooled to 0° C. to complete the crystallization and the crystals were filtered from the mother liquor. The remaining crude mixture was adsorbed onto silica gel for flash chromatography (0 to 30% ethyl acetate/hexanes) to afford 91% of the desired 4-hydroxymethylbenzadehyde product as a white solid.

4-(Triisopropylsiloxy)methylbenzaldehyde: The triisopropylsilyl protection began by preparing a suspension of 4-hydroxymethylbenzaldehyde (MW 136.15, 13.66 mmol, 1.86 g, 1 eq) in dichloromethane (20 mL) at room temperature. To this suspension was added imidazole (MW 68.08, 27.32 mmol, 1.86 g, 2 eq) and triethylamine (5 mL). Triisopropylchlorosilane (MW 192.80, 15.03 mmol, 2.89 g, 3.2 mL, 1.1 eq) was added in one portion, and the reaction was allowed to stir at room temperature for one hour. The disappearance of starting material was monitored by TLC (20% EtOAc/hexane). At the end of the reaction, an aqueous sodium bicarbonate solution was added and the mixture was shaken in a separatory funnel. The aqueous and organic layers were separated, and the organic layer was extracted (3×20 mL) with ethyl acetate. The organic layers were combined, dried with sodium sulfate, and concentrated under reduced pressure. The resulting organic residue was dissolved in the minimum amount of dichloromethane and was filtered through silica gel to remove the baseline polar material. The eluted organic solution was adsorbed onto silica and purified using chromatography (0 to 35% DCM/hexanes) to give a 90% yield of the desired TIPS-protected benzyl ether.

4,4-Difluoro-1,3,5,7-tetramethyl-8-(4'-(triisopropylsiloxy)methylphenyl)-4-bora-3a,4a-diaza-s-indacene: To a solution of the O-TIPS (O-triisopropylsilyl) protected benzaldehyde (MW 278.41, 13.66 mmol, 3.80 g, 1 eq) in dichloromethane (50 mL) at room temperature, 2,4-dimethylpyrrole (MW 95.14, 27.32 mmol, 2.59 g, d 0.924, 2.81 mL) was added. In a dropwise fashion, trifluoroacetic acid (MW 114.02, 1.36 mmol, 0.149 g, d 1.49, 100 uL, 0.1 eq) was added and the reaction was allowed to stir at room temperature overnight (about 10 hours). To this stirring reaction, 2,3-dichloro-5,6-dicyanobenzoquinone (DDQ) (MW 227, 13.66 mmol, 3.10 g, 1 eq) was added in one portion, and the reaction was allowed to continue to stir for an additional hour at room temperature. After the oxidation to the dipyrromethene intermediate was completed, triethylamine (MW 101.19, 136.6 mmol, 5.34 g, d 0.742, 7.2 mL, 5 eq) was added and the reaction stirred for 10 minutes. The reaction turned from a dark red to dark green color when this base was added. After waiting 10 minutes, the reaction was cooled to 0° C., and boron trifluoride diethyletherate ($BF_3 \cdot OEt_2$) (MW 141.93, 68.30 mmol, 9.69 g, d 1.13, 8.5 mL) was added in a dropwise fashion. The reaction color changed from green to dark red, and the reaction was allowed to warm to room temperature and stir for 3 more hours. The reaction was the poured into a separatory funnel half filled with saturated sodium bicarbonate solution. The contents were shaken vigorously, and the organic and aqueous layers were separated. The aqueous layer was extracted (3×20 mL) with ethyl acetate, and the combined organic layers were dried with sodium sulfate and concentrated under reduced pressure. The red residue was purified using flash chromatography (0 to 50% DCM/hexane) to produce the desired boron dipyrromethene (BP) dye in 32% yield as an orange solid.

3-12'-(4"-N,N-dibutylaminophenyl)ethenyl)-4,4-difluoro-8-(4'-(triisopropylsiloxy)methylphenyl)-1,5,7-trimethyl-4-bora-3a,4a-diaza-s-indacene: A solution of the above BP dye was stirred in toluene under an argon atmosphere. 4-N,N-dibutylaminobenzaldehyde (1 eq), p-toluenesulfonic acid (2 eq), and piperidine (2 eq) were added. The reaction was heated to reflux (about 115° C.) and the reaction was allowed to stir at the temperature for 6 hours. The disappearance of the red starting material and formation of the dark blue product was observed by TLC in 30% DCM/hexane. At the end of the condensation, the reaction was cooled to room temperature and emptied to a separatory funnel half-filled with deionized water. Ethyl acetate (20 mL) were added, and the contents were vigorously shaken. The aqueous and organic layers were separated, and the aqueous layer was extracted (3×10 mL) with ethyl acetate. The combined organic layers were dried with sodium sulfate, and concentrated under reduced pressure. The black residue was adsorbed onto silica gel and purified by flash chromatography (Combiflash unit, 0 to 50% DCM/hexane) to isolate 88.5 mg of the desired condensed BP dye as a navy blue solid in 67% yield.

3-{2'-(4"-N,N-dibutylaminophenyl)ethenyl}-4,4-difluoro-8-(4'-hydroxymethylphenyl)-1,5,7-trimethyl-4-bora-3a,4a-diaza-s-indacene: Triethylamine trihydrofluoride (10 eq) was added to the above BP compound (1 eq) in tetrahydrofuran and stirred at room temperature for 4 hours. The reaction mixture was adsorbed directly onto silica gel and purified via by flash chromatography (CombiFlash unit), eluting the pure product with 1/1 hexane/ethyl acetate.

3-{2'-(4"-N,N-dibutylaminophenyl)ethenyl}-4,4-difluoro-8-(4% (methanesulfonoxy)methylphenyl)-1,5,7-trimethyl-4-bora-3a,4a-diaza-s-indacene: The above BP was dissolved in dichloromethane and then deprotonated with Huenig's base (4eq). This solution was then cooled to 0° C. and thoroughly sparged with argon. Methanesulfonyl chloride (1.25 eq) was then added to the reaction mixture and the contents were allowed to stir overnight. The reaction mixture was then absorbed onto silica gel and chromatographed through a silica gel column using a hexane/ethyl acetate gradient to afford pure material.

3-{2'-(4"-N,N-dibutylaminophenyl)ethenyl}-4,4-difluoro-8-(4'-(N-ethyl-N,N-dimethylammonium)methylphenyl)-1,5,7-trimethyl-4-bora-3a,4a-diaza-s-indacene: The above BP dye was dissolved in dichloromethane. A large excess (10 eq) of N,N-dimethyl-N-ethylamine was then added and the reaction was allowed stir at room temperature. The reaction mixture was monitored for completeness by TLC (1/1 hexane/ethyl acetate). After overnight reaction, the reaction mixture was evaporated almost to dryness, then washed with MTBE. The precipitated material was collected and dissolved in a minimum volume of methanol, then re-precipitated with a large excess of MTBE. This precipitate was collected and kept away from light and stored in the refrigerator (4° C.).

Example 3

This example describes the synthesis of 1-3. The synthesis is shown in Scheme 3.

Scheme 3. Synthesis of I-3

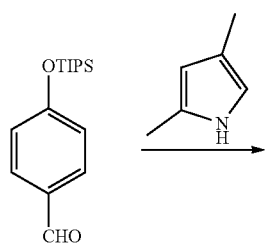

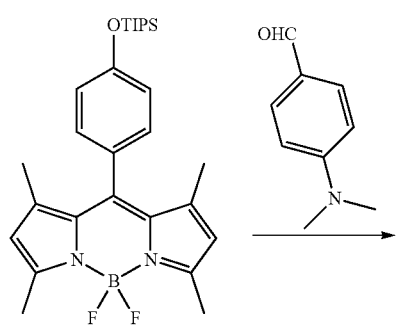

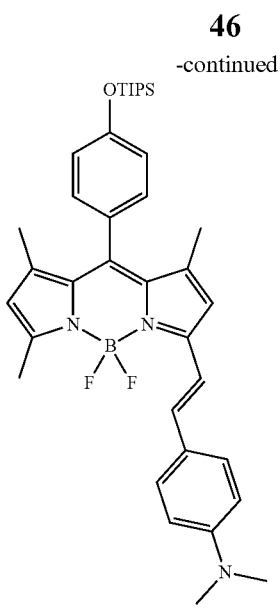

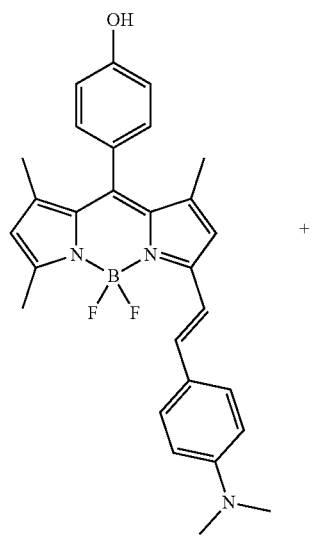

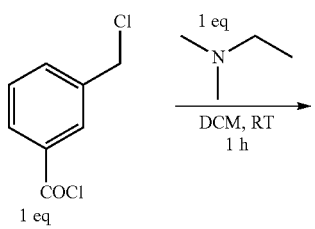

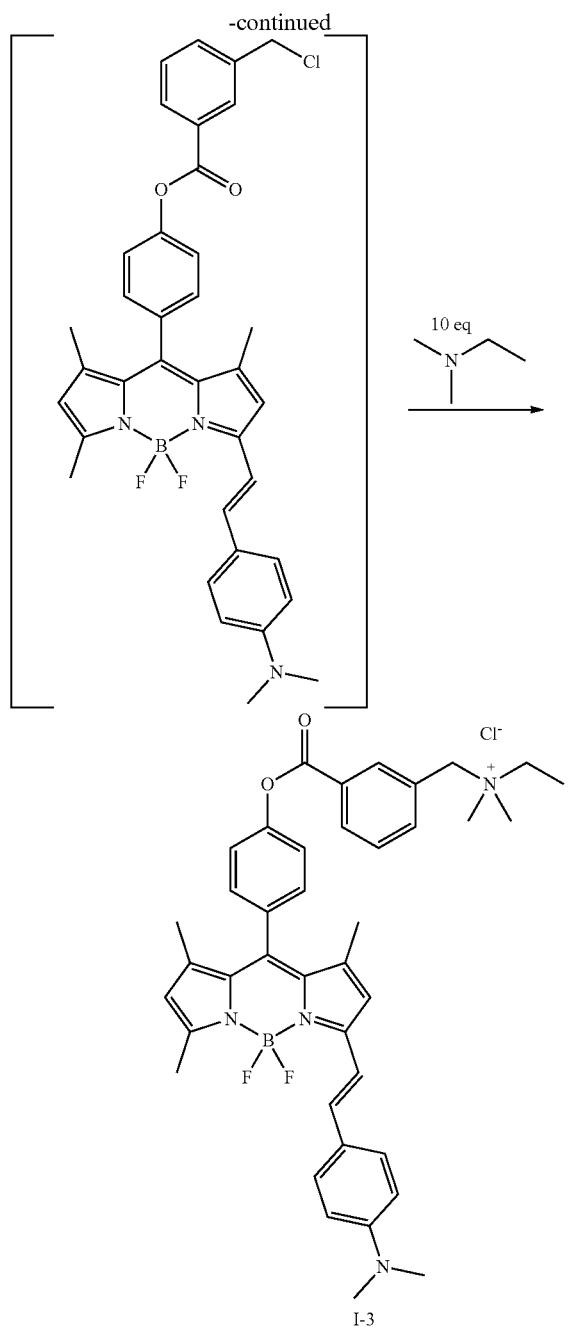

ness. The residue was chromatographed on silica gel, eluting the expected product with 7/1 hexanes/ethyl acetate. The BP dye was synthesized as expected in moderate yield (22%; 1 g).

BP dye (MW 496.52; 375 mg; 0.76 mmol; 1 eq), N,N-dimethylaminobenzaldehyde (MW 149.19; 113 mg; 0.76 mmol; 1 eq), piperidine (500 uL) and p-TsOH (several crystals) were dissolved in toluene (15 mL) along with several 4 A molecular sieves. The reaction flask was fitted with multiple condensers. The reaction temperature was raised to 130° C. and the reaction mixture was allowed to reflux overnight. Following overnight, the reaction mixture was allowed to cool to room temperature. The crude material was washed into a 250 mL RB flask and then adsorbed onto silica gel. After thoroughly drying the adsorbed material, it was purified by silica gel chromatography eluting the desired mono-coupled product with 10% ethyl acetate. TiPS-protected BP (MW 627.69; 208 mg; 0.33 mmol; 1 eq) was dissolved in 40 mL THF and stirred. To this solution was added dropwise TREAT-HF (MW 161.21; 336 mg; d 0.99; 20 eq; 334 uL). The deep blue solution was stirred at room temperature and monitored via TLC (4/1 hexane/ethyl acetate) for completeness. Reaction mixture was adsorbed directly onto silica gel and purified by silica gel chromatography, eluting the pure product with 1/1 (hexane/ethyl acetate).

BP dye (MW 471.35; 51 mg; 0.1 mmol; 1 eq) was stirred in DCM (5 mL) at room temperature. 3-Chloromethylbenzoyl chloride (MW 189.04; 19 mg; d 1.33; 0.1 mmol; 1 eq; 15 uL) and dimethylethylamine (MW 73.14; 7 mg; d 0.675; 0.1 mmol; 1 eq; 11 uL) were added and the reaction was stirred at room temperature for 1 h. TLC at 1 h indicated that most starting material had been converted to the benzoate intermediate. A further 10 eq of DMEA (100 uL) were then added and the reaction was allowed to continue at room temperature. Following overnight, the reaction mixture was concentrated under reduced pressure and low heat. A large excess of MTBE was then added to precipitate the charged compound. The material was isolated by filtration and dissolved in methanol. The methanol was removed and the material was then dissolved in DCM and filtered through a 100 nm syringe filter.

Example 4

This example describes the synthesis of I-4. The synthesis is shown in Scheme 4.

Scheme 4. Synthesis of I-4

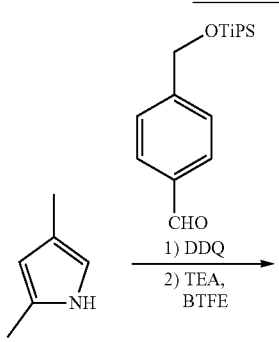

2,4-Dimethylpyrrole (MW 95.15; 1.85 g; d 0.924; 19 mmol; 2 eq; 2 mL) and 4-tri(isopropyl)silylether benzaldehyde (MW 278.46; 2.7 g; 9.7 mmol; 1 eq) were dissolved in 100 mL dichloromethane under Argon atmosphere. Two drops of TFA were added and the solution stirred at room temperature overnight. Following overnight, DDQ (MW 227.01; 2.2 g; 9.7 mmol; 1 eq) was added and stirring was continued for another 75 min. Under argon sparge, triethylamine (MW 101.19; 4.9 g; d 0.726; 49 mmol; 5 eq; 6.8 mL) and boron trifluoride diethyl etherate solution (MW 141.93; 9.6 g; d 1.13; 68 mmol; 7 eq; 8.5 mL) were added and the reaction mixture was allowed to stir at room temperature. After stirring for 120 min, the reaction mixture was neutralized with a minimum volume of sodium bicarbonate solution, dried over sodium sulfate and evaporated to dry-

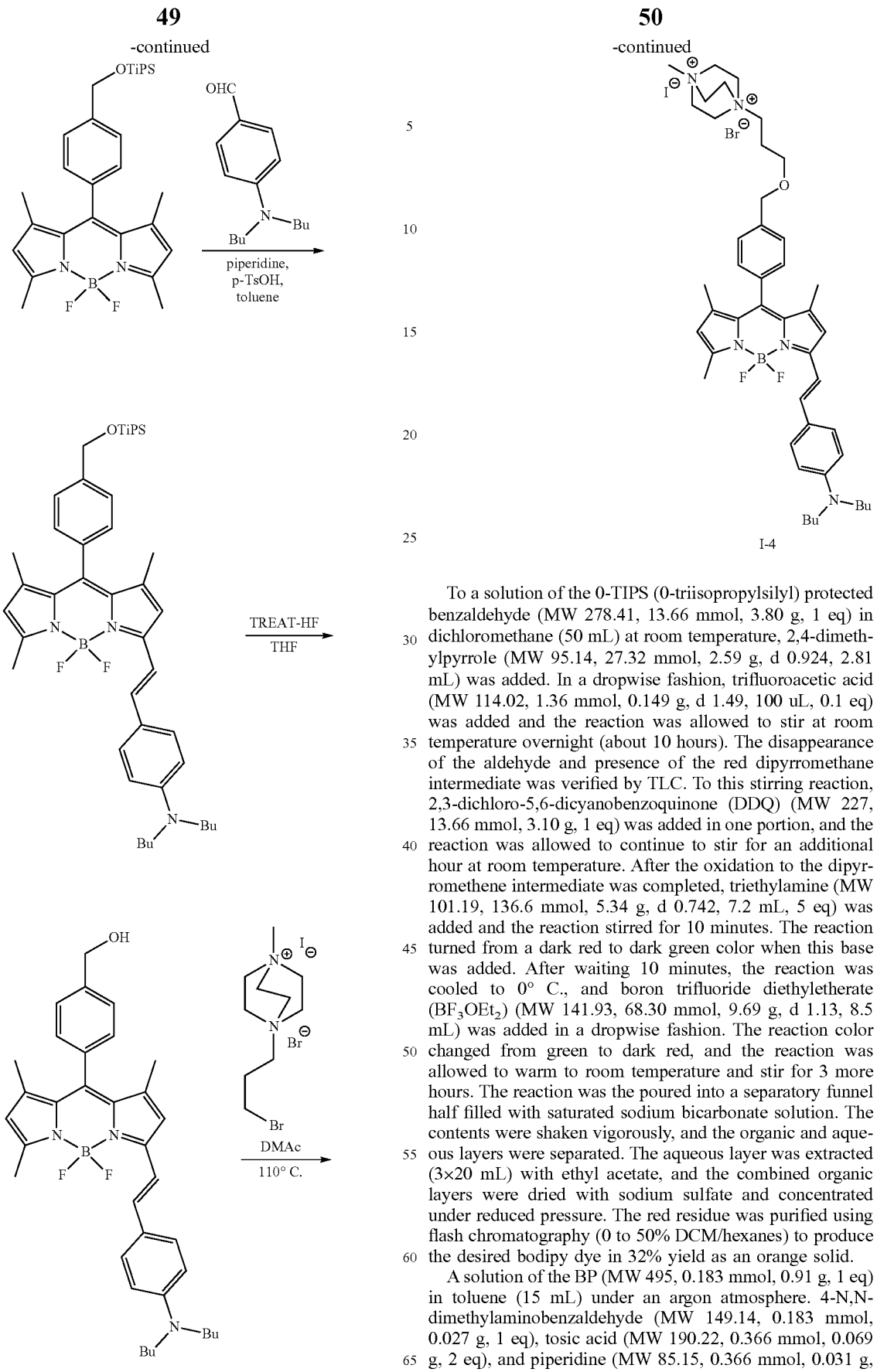

To a solution of the 0-TIPS (0-triisopropylsilyl) protected benzaldehyde (MW 278.41, 13.66 mmol, 3.80 g, 1 eq) in dichloromethane (50 mL) at room temperature, 2,4-dimethylpyrrole (MW 95.14, 27.32 mmol, 2.59 g, d 0.924, 2.81 mL) was added. In a dropwise fashion, trifluoroacetic acid (MW 114.02, 1.36 mmol, 0.149 g, d 1.49, 100 uL, 0.1 eq) was added and the reaction was allowed to stir at room temperature overnight (about 10 hours). The disappearance of the aldehyde and presence of the red dipyrromethane intermediate was verified by TLC. To this stirring reaction, 2,3-dichloro-5,6-dicyanobenzoquinone (DDQ) (MW 227, 13.66 mmol, 3.10 g, 1 eq) was added in one portion, and the reaction was allowed to continue to stir for an additional hour at room temperature. After the oxidation to the dipyrromethene intermediate was completed, triethylamine (MW 101.19, 136.6 mmol, 5.34 g, d 0.742, 7.2 mL, 5 eq) was added and the reaction stirred for 10 minutes. The reaction turned from a dark red to dark green color when this base was added. After waiting 10 minutes, the reaction was cooled to 0° C., and boron trifluoride diethyletherate (BF$_3$OEt$_2$) (MW 141.93, 68.30 mmol, 9.69 g, d 1.13, 8.5 mL) was added in a dropwise fashion. The reaction color changed from green to dark red, and the reaction was allowed to warm to room temperature and stir for 3 more hours. The reaction was the poured into a separatory funnel half filled with saturated sodium bicarbonate solution. The contents were shaken vigorously, and the organic and aqueous layers were separated. The aqueous layer was extracted (3×20 mL) with ethyl acetate, and the combined organic layers were dried with sodium sulfate and concentrated under reduced pressure. The red residue was purified using flash chromatography (0 to 50% DCM/hexanes) to produce the desired bodipy dye in 32% yield as an orange solid.

A solution of the BP (MW 495, 0.183 mmol, 0.91 g, 1 eq) in toluene (15 mL) under an argon atmosphere. 4-N,N-dimethylaminobenzaldehyde (MW 149.14, 0.183 mmol, 0.027 g, 1 eq), tosic acid (MW 190.22, 0.366 mmol, 0.069 g, 2 eq), and piperidine (MW 85.15, 0.366 mmol, 0.031 g, d 0.865, 0.036 mL, 2 eq) were added. The reaction was heated to reflux (about 115° C.) and the reaction was allowed to stir at the temperature for 15 hours. The disappearance of the red starting material and formation of the dark blue product was observed by TLC in 30% DCM/hexanes. At the end of the condensation, the reaction was cooled to room temperature and emptied to a separatory funnel half-filled with deinonized water. Ethyl acetate (20 mL) were added, and the contents were vigorously shaken. The aqueous and organic layers were separated, and the aqueous layer was extracted (3×10 mL) with ethyl acetate. The combined organic layers were dried with sodium sulfate, and concentrated under reduced pressure. The black residue was adsorbed onto silica gel and chromatographed (0 to 50% DCM/hexanes) to isolate 88.5 mg of the desired condensed BP as a navy blue solid in 67% yield.

BP (MW 725.88; 124 mg; 0.17 mmol; 1 eq) was dissolved in 5 mL THF and stirred under argon atmosphere. TREAT-HF (MW 161.21; 275 mg; d 0.99; 10 eq; 278 uL) was then added and the reaction mixture was stirred overnight at room temperature. The crude reaction mixture was adsorbed directly onto silica gel, the silica gel was dried under reduced pressure and the product was purified by silica gel chromatography. BP (MW 569.54; 27 mg; 47 umol; 1 eq) and potassium carbonate (MW 138.99; 0.1 mmol; 20 mg; 3 eq) were stirred together in toluene (3 mL) for 15 min, the 1-bromopropyl-4-methyl-1,4-diazoniabicyclo[2.2.2]octane salt (MW 456.00; 214 mg; 0.47 mmol; 10 eq) was added and all reagents were stirred in a 2/1 toluene/dimethylacetamide (5 mL) solution at 110 C overnight. Reaction mixture was allowed to cool to room temperature and solvents were removed under reduced pressure. Crude product was dissolved in 1 mL acetonitrile and then precipitated with MTBE. Precipitate was collected, analyzed by UV-vis and fluorescence emission spectroscopy.

Example 5

This example describes the synthesis of 1-5 and 1-6. The synthesis is shown in Scheme 5.

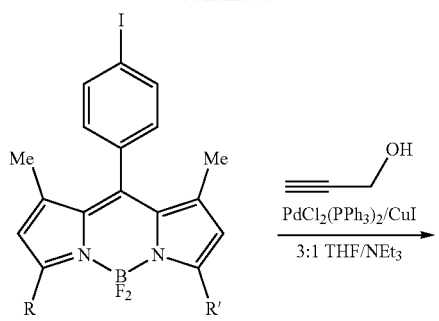

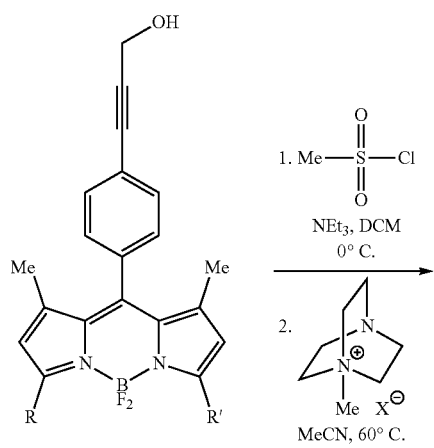

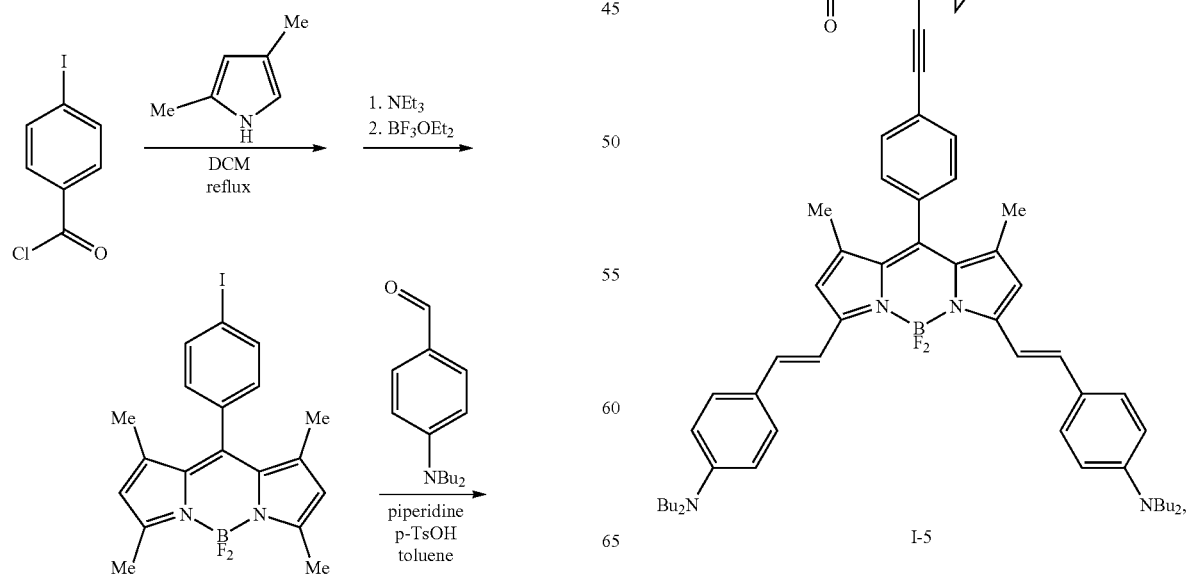

-continued

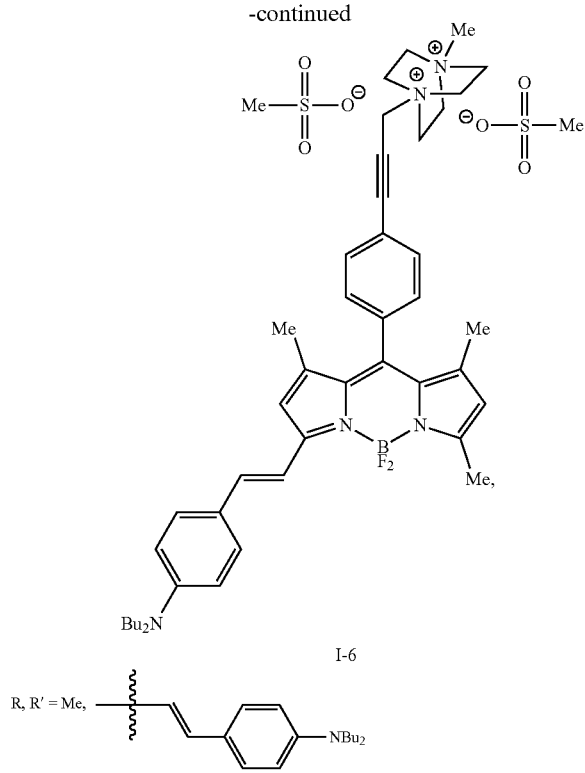

I-6

R, R' = Me, 8-iodophenyl-1,3,5,7-tetramethyl BP: A 500 mL 3 neck Morton flask with high efficiency condenser was charged with a stir bar, 250 mL degassed dichloromethane, 5.33 g 4-iodobenzoyl chloride, and 3.85 g 2,4-dimethylpyrrole then refluxed 3 hours. Initially the reaction was a white-yellow suspension that became clear red while refluxing. The hot water bath was removed with the argon flow increased, and the reflux stopped. Room temperature water was added to the bath. 14 mL trimethylamine was added via syringe and needle through a septum over 2 minutes. After the addition the reaction was stirred 5 minutes then 17.5 mL boron trifluoride diethyletherate was added dropwise over 5 minutes via addition funnel. The reaction was refluxed for 1 hour in a 50° C. water bath from 5 μm to 6 pm then water bath drained and the reaction allowed to stir at room temperature overnight. TLC shows a BP dye. 100 mL water was carefully added and stirred vigorously 10 minutes. The organic layer was pushed out and dried over anhydrous sodium sulfate, decanted, rinsed with 5×50 mL dichloromethane, stripped, then run on a silica column in 1:1 hexane/DCM. The material was dissolved in 100 mL DCM, washed with 100 mL water, separated and the organic layer absorbed onto 25 g silica. Chromatography was done on a 40 gram column, and a gradient from 100% hexanes to 1:1 hexanes DCM, the pure dye collected (verified by TLC), stripped on rotavap then high vacuum overnight (0.15 torr), 3.7 grams (41% yield).

Mono-addition of Knoevenagel condensation: A 50 mL 3-neck flask with stir bar, Vigreux column, argon, oil bath, is charged with 455 mg Iodophenyl-BP, 115 mg dibutylaminobenzaldehyde, 24 mL toluene, 0.25 mL piperidine and a crystal of p-TsOH-H2O. Reaction was refluxed overnight. The reaction was cooled, stripped, and run on 5.75 g silica with DCM, stripped again, chromatographed with a gradient to 40% DCM in hexanes. The product was stripped, high vacuum dried, yield=70 mg (21% based on aldehyde).

Sonogashira coupling of propargyl alcohol to BP: A 4 mL vial was charged with 49 mg BP, 4 mg PdCl2(PPh3)2, 2 mg CuI, stir bar, septum, purged with argon then added 1 mL degassed 3:1 THF/NEt3 and 10 uL propargyl alcohol, stirred at room temperature for 1 hour. Work up: 10 mL water and 10 mL DCM, layers separated, extracted water 2×5 mL DCM, combine organic layers, dried over anhydrous sodium sulfate, stripped, silica plug using 100% DCM gradient to 5% methanol and collected product, stripped, high vacuum dried, N=42 mg (MW=378) quantitative yield.

Mesylation of BP-coupled propargyl alcohol: A 4 mL vial was charged with 42 mg BP and a stir bar. Septum was added and placed under argon. 1 mL tetrahydrofuran and 15 uL triethylamine was added then cooled in an ice bath. 10 uL (15 mg) methanesulfonyl chloride was added via gas tight syringe. Stirred 1 hour and an additional 3 uL triethylamine and 5 uL methanesulfonyl chloride added and stirred 1 hour. The reaction was stripped on the rotavap, silica plug with DCM, eluted product, pure fractions stripped, high vacuum overnight. Yield=14 mg (red solid thin film, MW=456) (28%)

Dicationic VSD: 14 mg BP was transferred to a 16 mL vial using 2×0.5 mL acetonitrile, 8 mg Me-DABCO-I, stirred at room temperature. Heated to 60° C. in an oil bath and red precipitate formed. Stirred one hour at 60° C. and then cooled to room temperature. Decanted the acetonitrile, washed with 0.5 mL acetonitrile, decanted, then 2 mL MTBE added, washed, decanted and high vacuum dried the solid 1 hour, N=6 mg. MW=710. Yield=27%. Product is water soluble and will not go into DCM layer from the water layer.

Example 6

This prophetic example describes the synthesis of 1-7. The synthesis is shown in Scheme 6, wherein $R^1$ and $R^2$ are as described herein.

Scheme 6. Synthesis of I-7.

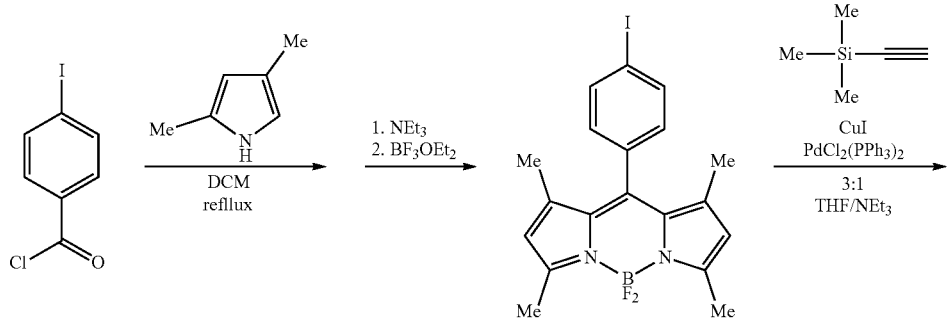

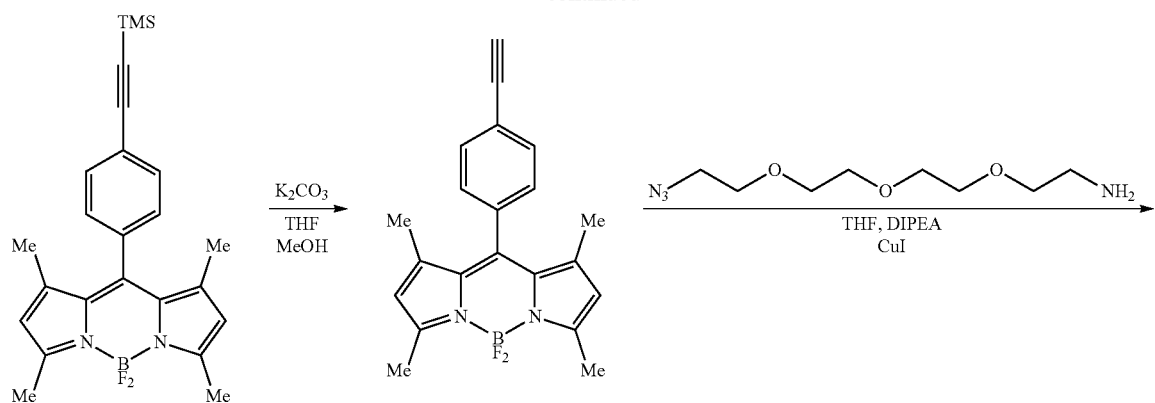
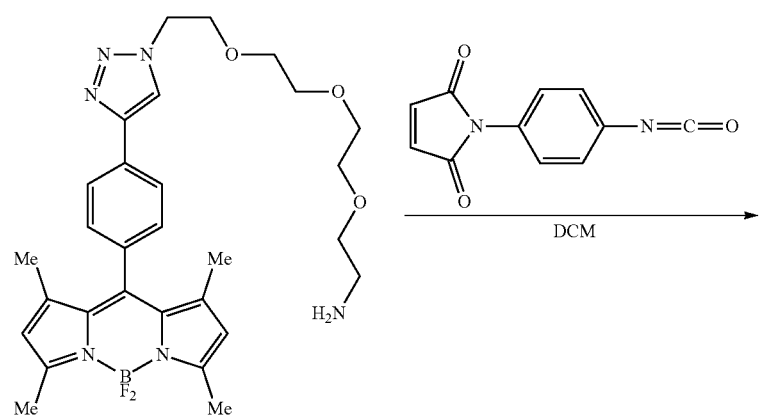
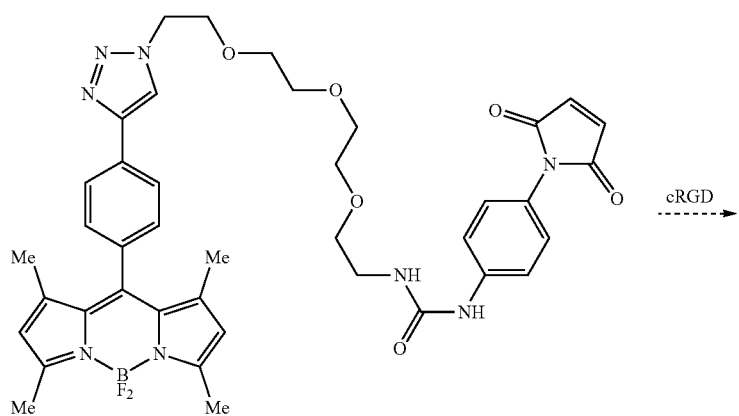

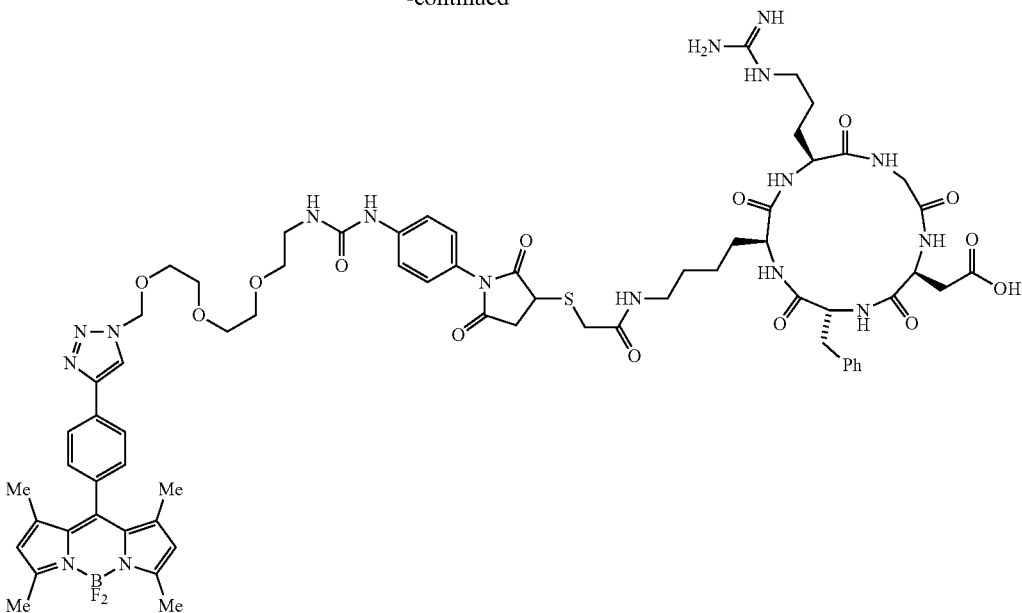

I-7

8-iodophenyl-1,3,5,7-tetramethyl BP: was synthesized as described in Example 5.

Mono-addition of Knoevenagel condensation: A 50 mL 3-neck flask with stir bar, Vigreux column, argon, oil bath, is charged with 455 mg Iodophenyl-BP, 115 mg dibutylaminobenzaldehyde, 24 mL toluene, 0.25 mL piperidine and a crystal of p-TsOH-H2O. Reaction was refluxed overnight. The reaction was cooled, stripped, 5.75 g silica with DCM, stripped again, Combiflash purified hexane gradient to 40% DCM in hexanes, most of the mono was separated from the starting material. Stripped, high vacuum dried, yield=70 mg (21% based on aldehyde).

Sonogashira coupling of trimethylsilylacetylene to BP and subsequent basic deprotection: A 4 mL vial was charged with 49 mg BP, 4 mg PdCl2(PPh3)2, 2 mg CuI, stir bar, septum, purged with argon then added 1 mL degassed 3:1 THF/Net3 and 10 uL trimethylsilylacetylene (TMSA), stirred at room temperature for 1 hour. Work up: 10 mL water and 10 mL DCM, layers separated, extracted water with 2×5 mL DCM, combine organic layers, dried over anhydrous sodium sulfate, stripped, silica plug using 100% DCM gradient to 5% methanol and collected product, stripped, high vacuum dried, N=42 mg (MW=378) quantitative yield. The phenylacetylene BP (0.5 mmol TMS-acetylene-BODIPY), 140 mg potassium carbonate (1 mmol, 2 equiv), 5 mL tetrahydrofuran and 5 mL methanol stirred overnight under argon. 0.5 mL water was added, stirred 30 minutes then syringe filtered and stripped. Silica column/plug 1:1 DCM/Hex run, product collected, stripped, high vacuum, obtained 57% yield.

Click Coupling of Phenylacetylene BP and N3-PEG-NH2: Using click chemistry, the BP alkyne was coupled to an azide-PEG-amine forming a triazole. A 4 mL vial charged with 2.5 mL THF and 0.25 mL DIPEA was degassed with argon vigorously for 10 minutes. A separate 4 mL vial was charged with 35 mg alkyne-BP, 3 mg CuI and a stir bar then purged with argon. 20 uL (22 mg) of azidePEG-NH2 (TCI) was injected into the THF/DIPEA, degassed briefly then injected into the reaction vial followed by degassing for 1 minute and the orange-red solution was allowed to stir overnight under argon. Reaction stripped and a silica plug/column was used eluting with 10% methanol in DCM, a red forecut was taken, the product eluted continuously even with 50% methanol and 100% methanol. Added 1% 63rimethylamine, 10% methanol in DCM and immediately eluted completely. The product was stripped, dried under high vacuum, 46 mg (81% yield, MW=566).

Urethane coupling between Amine-labeled BP and Isocyanate-Phenylmaleimide: 4 mL vial charged with stir bar, 57.5 mg BP by 3×1 mL DCM transfer with pipet then argon purged/vented which evaporated the DCM down to 1.5 mL. 22 mg p-isocyanate-phenyl-maleimide dissolved in 1 mL DCM in a separate 4 mL vial then added dropwise to reaction via syringe and needle. The reaction was loaded onto a silica plug and eluted with gradient 5-10% MeOH in DCM, product collected, stripped, high vacuum overnight. Vacuum (0.5 torr) released, yield=70 mg, 89%. [MW=781, theoretical yield=79 mg]

Cysteine-labeled cRGD coupling to maleimide-BP: Under slightly basic conditions (pH 7.1-7.4), 2 eq of cysteine-labeled cRGD were stirred with 1 eq of maleimide-BP to form peptide-BP conjugate.

Example 7

This example describes the synthesis of 1-9. The synthesis is shown in Scheme 7.

Scheme 7. Synthesis of I-9.

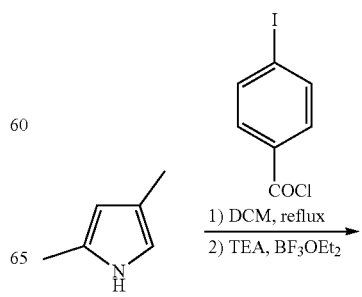

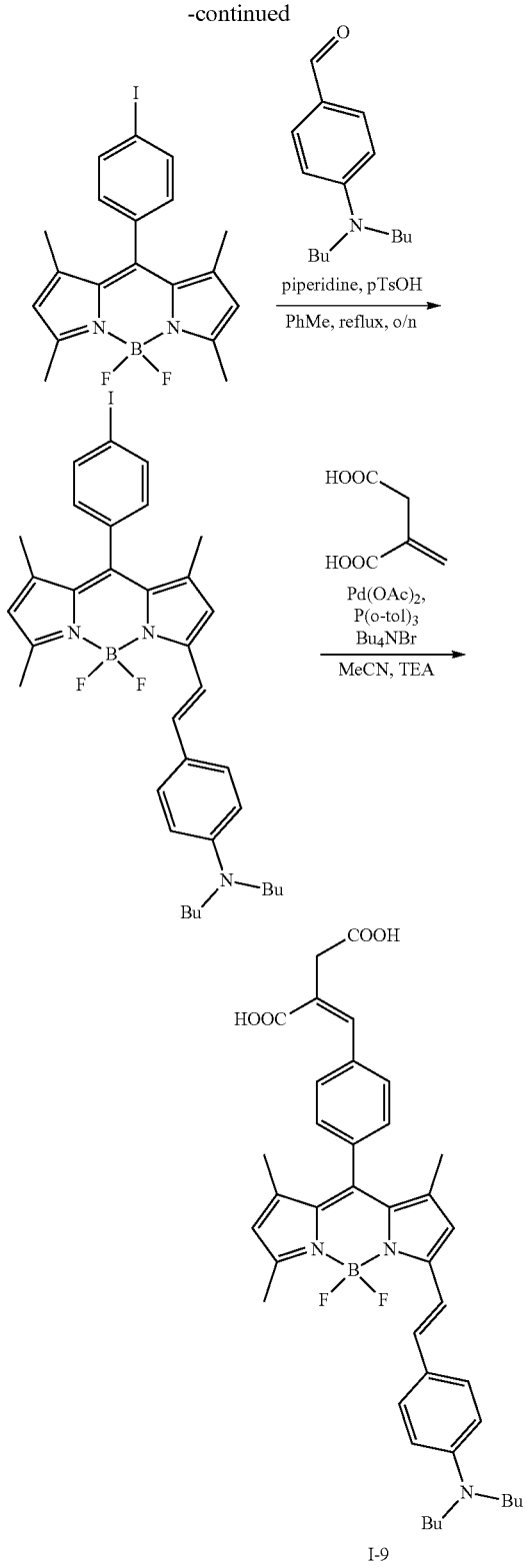

I-9

Heck coupling between iodophenyl BP and itaconic acid was performed. BP (133 mg) was added to a suitably-sized vial equipped with a stir bar. Palladium acetate (5 mg), tri(o-tolyl)phosphine (21 mg) and tetrabutylammonium bromide (65 mg) were added to the vial as dry reagents. Thoroughly degassed acetonitrile (2.5 mL) and triethylamine (0.5 mL) were added to the vial. Under an argon stream, itaconic acid (27 mg) was added to the vial. The vial was sealed and an inert atmosphere was maintained. Following 24 hours of reaction time, the crude reaction mixture was purified using C18 reverse phase silica gel, eluting with acetone. 1H NMR spectra were taken in deuterated DMSO and acetone in order to confirm structure. 31 mg of pure material were isolated following purification (23% yield).

Example 8

This example shows the influence of the electron donating group on absorbance wavelength, emission wavelength, and Stokes shift. The absorbance wavelength, emission wavelength, and Stokes shift of 1-3 was compared to a similar molecule (i.e., TIPSOBP) that lacked an electron donating group. The absorbance and fluorescence spectra of 1-3 and TIPSOBP were obtained in various solvents, including dichloromethane, toluene, and methanol. The spectra in dichloromethane as shown in FIG. 1. Dye 1-3 had longer absorbance and emission wavelengths than TIPSOBP and a longer Stokes shift as shown in FIG. 1.

Example 9

Figure 2:
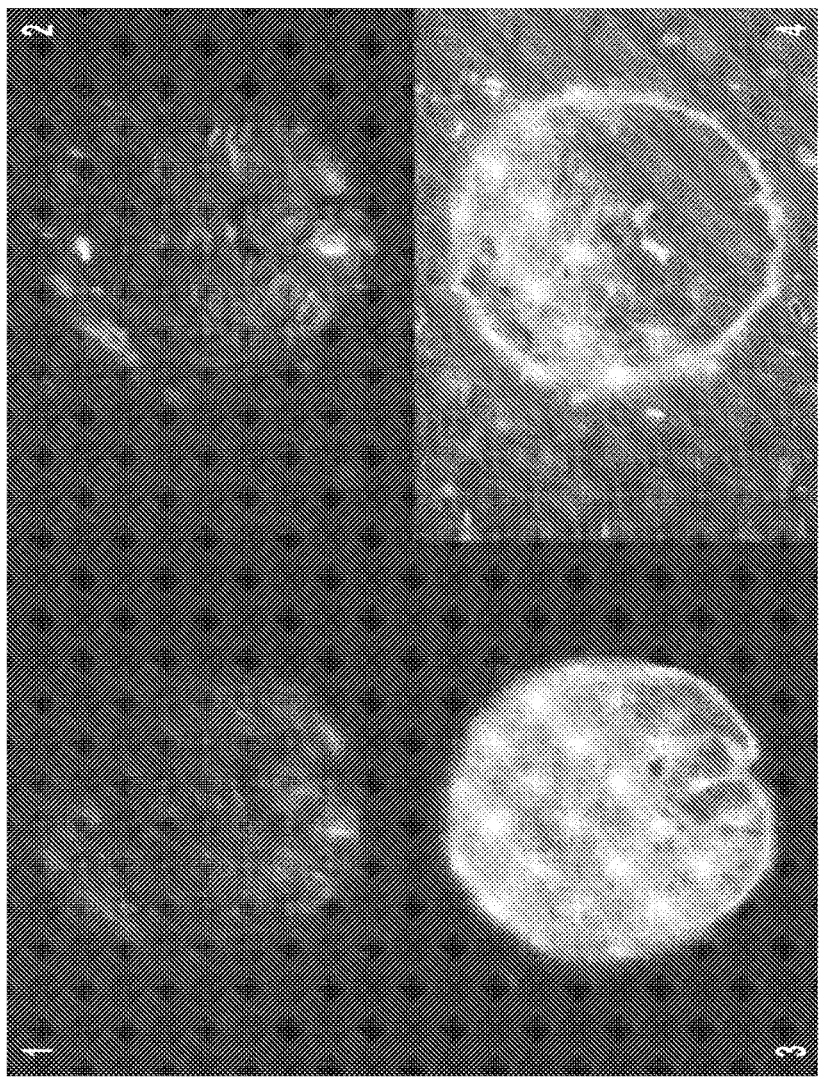
FIG. 2 shows fluorescent microscope images of a xenopus embryo stained with a voltage sensitive dye, according to certain embodiments.

This example describes the use of dye I-1 for voltage sensing. For use in voltage sensing, dye I-1 was dissolved in ethanol. Specifically, 0.35 mg of I-1 was dissolved in 200 ml of ethanol. Then, 25 ml of the dye in ethanol was then added to 5 ml of buffer containing stage 30 xenopus embryos. After 30 minutes of incubation, the embryos were imaged in an Olympus fluorescence microscope using a R6G/Texas Red filter set, and the images were acquired with a 12-bit camera and processed with Metamorph software. For membrane hyperpolarization and depolarization, either 4.5 mM KCl solution in buffer or 84.5 mM KCl solution, respectively, were added to petri dishes containing the embryos. Respective fluorescence imaging of the stained embryos are shown in FIG. 2. The images at the top are of the sample autofluorescence, using green light excitation; the autofluorescence is very similar before (left) and after (right) hyperpolarization with KCl. The images at the bottom are taken with yellow excitation light, which is absorbed by the dye and does not yield autofluorescence, and show that there is significantly more fluorescence from the cells after membrane hyperpolarization (left image, before hyperpolarization with KCl; right image after hyperpolarization with KCl.

Example 10

This example describes the synthesis of I-10. The synthesis is shown in Scheme 8.

Scheme 8. Synthesis of I-10

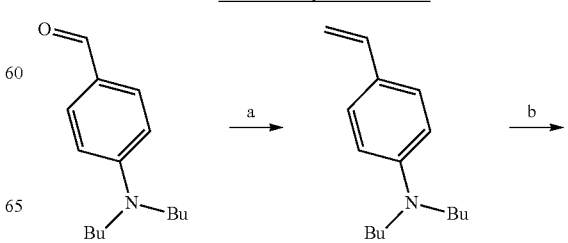

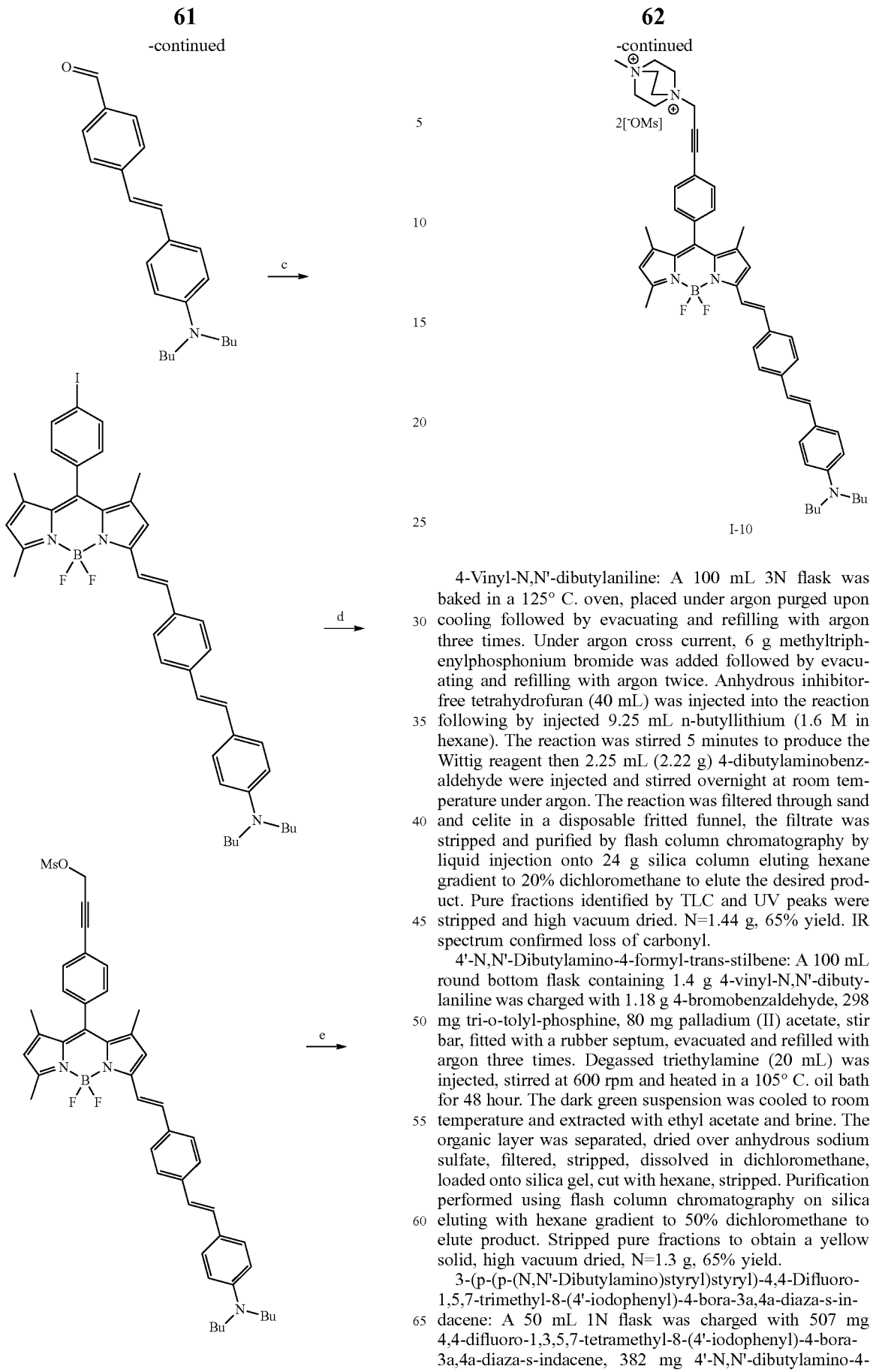

I-10

4-Vinyl-N,N'-dibutylaniline: A 100 mL 3N flask was baked in a 125° C. oven, placed under argon purged upon cooling followed by evacuating and refilling with argon three times. Under argon cross current, 6 g methyltriphenylphosphonium bromide was added followed by evacuating and refilling with argon twice. Anhydrous inhibitor-free tetrahydrofuran (40 mL) was injected into the reaction following by injected 9.25 mL n-butyllithium (1.6 M in hexane). The reaction was stirred 5 minutes to produce the Wittig reagent then 2.25 mL (2.22 g) 4-dibutylaminobenzaldehyde were injected and stirred overnight at room temperature under argon. The reaction was filtered through sand and celite in a disposable fritted funnel, the filtrate was stripped and purified by flash column chromatography by liquid injection onto 24 g silica column eluting hexane gradient to 20% dichloromethane to elute the desired product. Pure fractions identified by TLC and UV peaks were stripped and high vacuum dried. N=1.44 g, 65% yield. IR spectrum confirmed loss of carbonyl.

4'-N,N'-Dibutylamino-4-formyl-trans-stilbene: A 100 mL round bottom flask containing 1.4 g 4-vinyl-N,N'-dibutylaniline was charged with 1.18 g 4-bromobenzaldehyde, 298 mg tri-o-tolyl-phosphine, 80 mg palladium (II) acetate, stir bar, fitted with a rubber septum, evacuated and refilled with argon three times. Degassed triethylamine (20 mL) was injected, stirred at 600 rpm and heated in a 105° C. oil bath for 48 hour. The dark green suspension was cooled to room temperature and extracted with ethyl acetate and brine. The organic layer was separated, dried over anhydrous sodium sulfate, filtered, stripped, dissolved in dichloromethane, loaded onto silica gel, cut with hexane, stripped. Purification performed using flash column chromatography on silica eluting with hexane gradient to 50% dichloromethane to elute product. Stripped pure fractions to obtain a yellow solid, high vacuum dried, N=1.3 g, 65% yield.

3-(p-(p-(N,N'-Dibutylamino)styryl)styryl)-4,4-Difluoro-1,5,7-trimethyl-8-(4'-iodophenyl)-4-bora-3a,4a-diaza-s-indacene: A 50 mL 1N flask was charged with 507 mg 4,4-difluoro-1,3,5,7-tetramethyl-8-(4'-iodophenyl)-4-bora-3a,4a-diaza-s-indacene, 382 mg 4'-N,N'-dibutylamino-4- formyl-trans-stilbene, stir bar, 22 mL acetonitrile, 0.2 mL piperidine, 0.2 mL glacial acetic acid and a stir bar. The reaction was fitted with a Vigreux column with a gas adapter then evacuated and refilled with argon twice. With stirring, the reaction was heated in an oil bath 90° C. to reflux overnight. The reaction was cooled, stripped and dissolved in dichloromethane. UV-Vis spectrophotometry showed nearly equal distribution of unreacted starting material, mono- and bis-condensation products. Loaded onto silica gel, stripped, purified via flash column chromatography on 24 g silica, eluting with hexane gradient to 50% dichloromethane. The material could not be fully separated on silica and reverse phase C18 was needed. The solvent was stripped onto silica gel and placed on top of 12 g C18 silica and eluted with acetonitrile. Starting material eluted first, mono slowly and continuously eluted after, while the bis product did not elute. After 750 mL acetonitrile, stripped, high vacuum dried, N=84 mg, 10%.

3-(p-(p-(N,N'-Dibutylamino)styryl)styryl)-4,4-Difluoro-1,5,7-trimethyl-8-(p-(2-propyne-1-ol)phenyl)-4-bora-3a,4a-diaza-s-indacene: A 20 mL vial containing 77 mg of the BP synthesized in the previous step was charged with 5 mg dichlorobis(triphenylphosphine)palladium(II), 5 mg copper (I) iodide, stir bar, fitted with septum screw cap, evacuated and refilled with argon twice followed by argon purge. The reaction was injected with 3 mL degassed tetrahydrofuran and 1 mL degassed triethylamine and stirred. Then 15 uL propargyl alcohol was injected and with stirring, heated in a 60° C. oil bath for 1 hour and TLC showed complete reaction by TLC on silica with dichloromethane as compared to starting material. The reaction was stripped and purified via liquid injection using flash column chromatography with dichloromethane eluting hexane gradient to dichloromethane. Fractions containing product were stripped, high vacuum dried, N=50 mg, 71% yield.

3-(p-(p-(N,N'-Dibutylamino)styryl)styryl)-4,4-Difluoro-1,5,7-trimethyl-8-(p-(2-propyne-1-methylsulfonate)phenyl)-4-bora-3a,4a-diaza-s-indacene: An 8 mL vial was charged with stir bar and 50 mg previous BP was transferred via 4×1 mL dichloromethane, fitted with a septum screw cap, placed under argon, injected 20 uL triethylamine and 10 uL methanesulfonyl chloride at room temperature for 15 minutes. TLC on silica with dichloromethane showed reaction complete. The reaction was filtered onto 4 g silica plug and eluted with dichloromethane to produce a single spot material, stripped, high vacuum dried, N=56 mg, quantitative yield.

3-(p-(p-(N,N'-Dibutylamino)styryl)styryl)-4,4-Difluoro-1,5,7-trimethyl-8-(p-(2-propyne-1-(methyl(1,4-diazoniumbicyclo[2.2.2]octanyl))phenyl)-4-bora-3a,4a-diaza-s-indacene dimethylsulfonate salt: 56 mg of previous BP was transferred to a 10 mL 1 N 14/20 round bottom flask via 3×1 mL dichloromethane, stripped, high vacuum dried. Charged stir bar, 172 mg DABCO salt, 2 mL N,N-dimethylformamide, fitted with a rubber septum, argon, stirred in 80° C. oil bath 2 hours. As it cooled, 6 mL acetonitrile was added. The dye precipitated out of solution and transferred to a 60 mL centrifuge tube. The reaction was flask was rinsed with acetonitrile several times (25 mL total). The product was spun, decanted, washed 35 mL fresh acetonitrile, spun, decanted, washed with 30 mL diethyl ether, spun, decanted, high vacuum dried. The dye was transferred to a 4 mL vial, N=51 mg, 71% yield. TLC on silica with dichloromethane shows baseline material as expected and no starting material. 1H NMR in $CDCl_3$ was inconclusive although the material appeared to be fully soluble. 0.1 mL $CD_3OD$ was added to make approximately 9:1 $CDCl_3/CD_3OD$ and $^1H$ NMR was confirmed.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition of matter, comprising a compound of Formula I:

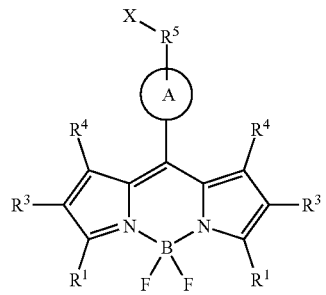

(I)

or a salt thereof, wherein:
   $R^1$ and $R^2$ are independently hydrogen, optionally substituted alkyl, or an electron donating group, provided that at least one of $R^1$ and $R^2$ is an electron donating group;
   each $R^3$ is independently hydrogen or optionally substituted alkyl;
   each $R^4$ is hydrogen or optionally substituted alkyl;
   Ring A is optionally substituted arylene or optionally substituted heteroarylene;
   $R^5$ is optionally substituted acylene, optionally substituted alkenylene, optionally substituted alkylene, optionally substituted alkynylene, substituted amino, optionally substituted arylene, optionally substituted heteroalkenylene, optionally substituted heteroalkylene, optionally substituted heteroalkynylene, optionally substituted heteroarylene, —O—, or optionally substituted thiolene;
   X is charged or has a log(P) of less than or equal to about 0;
   the electron donating group is —$(R^6)_n$—$R^7$:
   each $R^6$ is independently optionally substituted alkenylene, optionally substituted alkynylene, optionally substituted arylene, or optionally substituted heteroarylene;
   $R^7$ is —$N(R'')_2$ or optionally substituted thiol;
   each R" is independently $C_{1-12}$ alkyl, provided that at least one R" is $C_{2-12}$ alkyl; and
   n is 1-5.

2. The composition of claim 1, wherein $R^1$ and $R^2$ are independently hydrogen or an electron donating group.

3. The composition of claim 1, wherein $R^1$ and $R^2$ are independently optionally substituted alkyl or an electron donating group.

4. The composition of claim 1, wherein $R^1$ is an electron donating group.

5. The composition of claim 1, wherein $R^1$ is not an electron donating group.

6. The composition of claim 1, wherein the composition of matter has a fluorescent yield greater than or equal to 0.1.

7. A compound selected from the group consisting of:

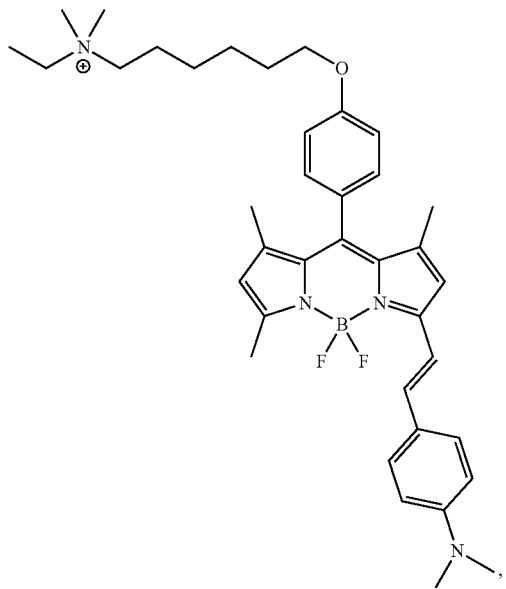

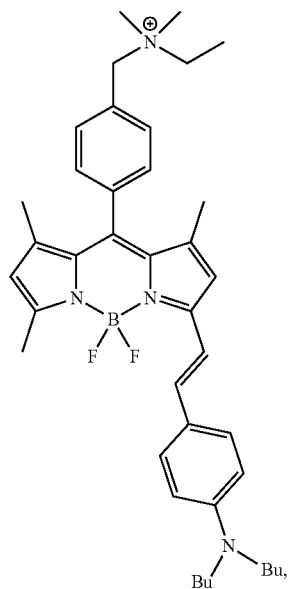

67
-continued
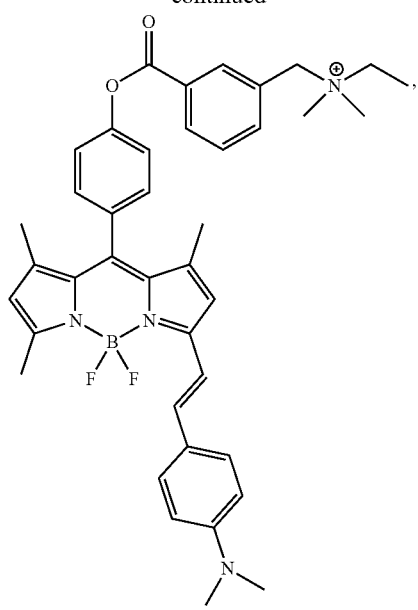
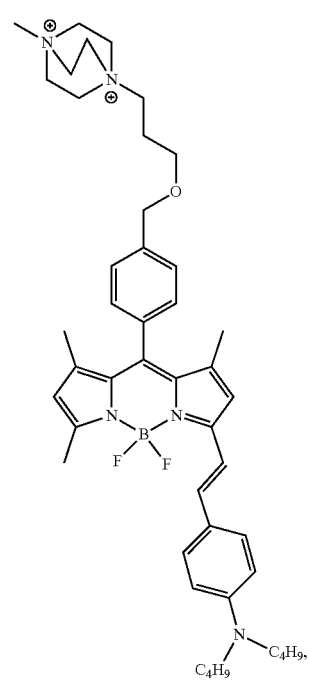
68
-continued
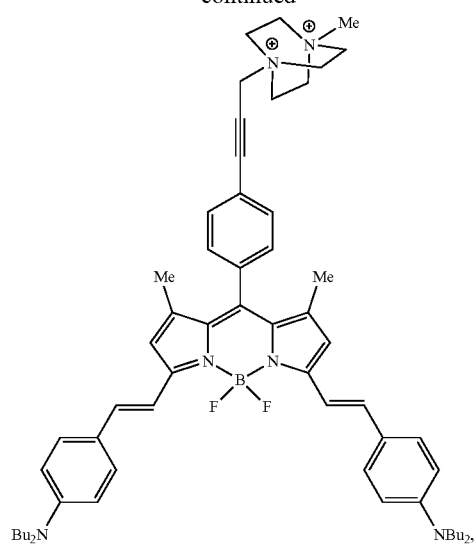
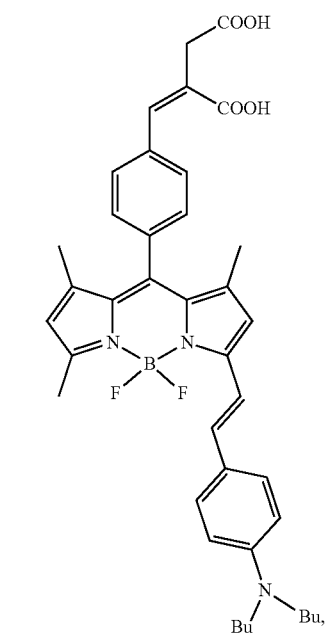

69
-continued
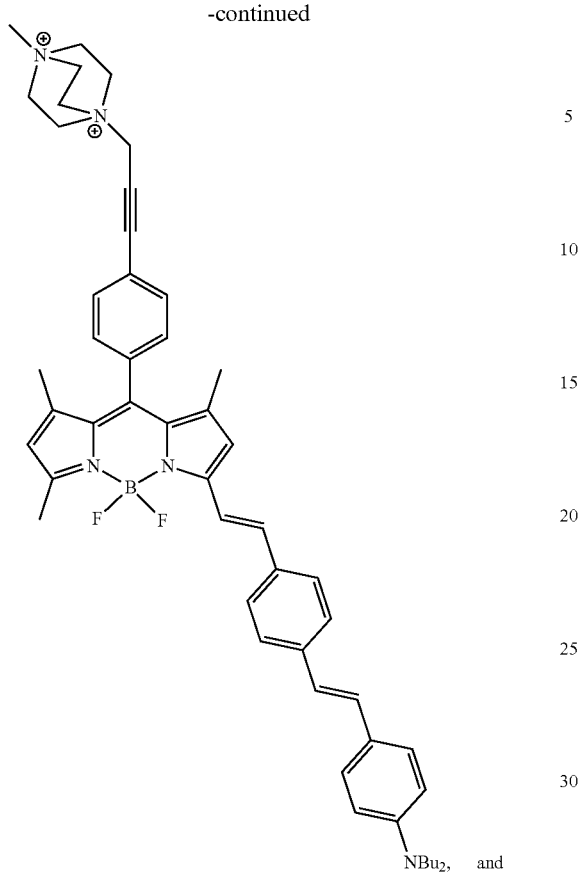
NBu₂, and
70
-continued
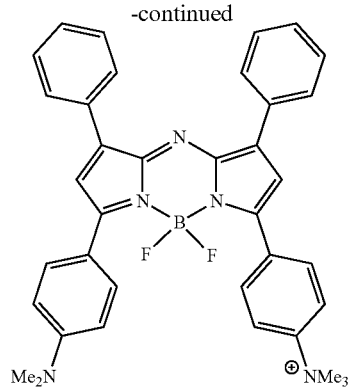
or a salt thereof.
* * * * *